US008063242B2

(12) United States Patent
Allegretti et al.

(10) Patent No.: US 8,063,242 B2
(45) Date of Patent: Nov. 22, 2011

(54) 2-ARYL-PROPIONIC ACIDS AND PHARMACEUTICAL COMPOSITIONS CONTAINING THEM

(75) Inventors: Marcello Allegretti, L'Aquila (IT); Riccardo Bertini, L'Aquila (IT); Cinzia Bizzarri, L'Aquila (IT); Maria Candida Cesta, L'Aquila (IT); Francesco Colotta, L'Aquila (IT)

(73) Assignee: Dompe PHA.R.MA S.p.A., L'Aquila (IT)

( * ) Notice: Subject to any disclaimer, the term of this patent is extended or adjusted under 35 U.S.C. 154(b) by 211 days.

(21) Appl. No.: 10/495,365

(22) PCT Filed: Nov. 19, 2002

(86) PCT No.: PCT/EP02/12939
§ 371 (c)(1),
(2), (4) Date: Jul. 7, 2004

(87) PCT Pub. No.: WO03/043625
PCT Pub. Date: May 30, 2003

(65) Prior Publication Data
US 2005/0038119 A1 Feb. 17, 2005

(30) Foreign Application Priority Data
Nov. 20, 2001 (IT) .............................. MI2001A2434

(51) Int. Cl.
A61K 31/192 (2006.01)

(52) U.S. Cl. ........ 562/468; 562/460; 562/459; 514/557; 514/553; 514/576

(58) Field of Classification Search .................. None
See application file for complete search history.

(56) References Cited

U.S. PATENT DOCUMENTS

| 3,629,320 A | * | 12/1971 | Wasley ........................... 560/12 |
| 3,766,263 A | | 10/1973 | Godfrey ........................ 260/520 |
| 4,465,855 A | * | 8/1984 | Palosi et al. .................... 562/496 |
| 4,720,506 A | | 1/1988 | Munakata et al. ............. 514/538 |
| 5,981,592 A | | 11/1999 | Wechter et al. ................ 514/570 |

FOREIGN PATENT DOCUMENTS

| BE | 621 255 A | 2/1963 |
| CA | 2362888 A1 | 8/2000 |
| DE | 25 33 397 A | 2/1976 |
| EP | 94599 A1 | 11/1983 |
| EP | 0 935 961 A | 8/1999 |
| ES | 415 446 A | 2/1976 |
| FR | 0006184 A | 2/2000 |
| GB | 1 132 318 A | 10/1968 |
| GB | 1 465 661 A | 2/1977 |
| GB | 1521906 A | 8/1978 |
| JP | 53007640 A | 1/1978 |
| WO | 98 09603 A | 3/1998 |
| WO | 00 06184 A | 2/2000 |
| WO | 01 58852 A | 8/2001 |

OTHER PUBLICATIONS

Haringman et al. Arthritis Res. Ther. 2004, 6, 93-97.*
Brancaccio et al J Med. Chem. 1981, 24, 998-1000.*
Derwent WPI, Section Ch. Week 197735, Derwent Publications Ltd., London, GB; AN 1977-61579Y, XP002236684 & JP 52 083822A (Jul. 13, 1977).
Brancaccio et al., J. Med. Chem., vol. 24, pp. 998-1000 (1981).
Atkinson et al., J. Med. Chem., vol. 26, pp. 1353-1360 (1983).
Rufer et al., European Journal of Medicinal Chemistry, Editions Scientifique Elsevier, Paris, FR., vol. 13, No. 2, pp. 193-198 (Mar. 1978).
Yorizumi, K., et al., "An Autopsy Case of Malignant Melanoma, Misdiagnosed as Pulmonary Cancer: Effect of Naproxen on Tumor Fever on Malignant Melanoma," IRYO, vol. 42, No. 4, pp. 357-362 (1988).
Kamper, A. L., et al., "Effects of Sulindac and Naproxen in Patients with Chronic Glomerular Disease," Scand. J. Rheumatology, pp. 26-31 (1986).
Burdick, K. H., et al., "Naproxen and Psoriasis," Arch. of Derma., vol. 112, No. 1, p. 121 (1976).
Jiang, W., et al., "Differential Effects of Naproxen on Ischemia and Reperfusion-Induced Excitation of Jejunal Afferents in the Anarsthetised Rat," Gastroenterology, vol. 114, No. 4, G3183 (1988).

* cited by examiner

Primary Examiner — Daniel Sullivan
Assistant Examiner — Yevegeny Valenrod
(74) Attorney, Agent, or Firm — Birch, Stewart, Kolasch & Birch, LLP

(57) ABSTRACT (R) and (S) 2-Aryl-propionic acids, and pharmaceutical compositions that contain them, are useful in inhibiting chemotactic activation of neutrophils (PMN leukocytes) induced by the interaction of Interleukin-8 (IL-8) with CXCR1 and CXCR2 membrane receptors. The acids are used for the prevention and treatment of pathologies deriving from said activation. In particular, the (R) enantiomers of said acids are lacking cyclo-oxygenase inhibition activity and are particularly useful in the treatment of neutrofil-dependent pathologies such as psoriasis, ulcerative colitis, melanoma, chronic obstructive pulmonary disease (COPD), bollous pemphigo, rheumatoid arthritis, idiopathic fibrosis, glomerulonephritis and in the prevention and treatment of damages caused by ischemia and reperfusion.

10 Claims, No Drawings

2-ARYL-PROPIONIC ACIDS AND PHARMACEUTICAL COMPOSITIONS CONTAINING THEM

This application is the National Stage of International Application number PCT/EP2002/012939 filed Nov. 19, 2002, which claims priority under 35 USC §119(a)-(d) of Application No. MI2001A002434 filed in Italy on Nov. 20, 2001.

BRIEF DESCRIPTION OF THE INVENTION

The present invention relates to (R,S) 2-aryl-propionic acids, their single enantiomers (R) and (S) and to pharmaceutical compositions containing them, which are used in the prevention and treatment of tissue damage due to the exacerbated recruitment of polymorphonucleated neutrophils (PMN leukocytes) at inflammation sites.

STATE OF THE ART

Particular blood cells (macrophages, granulocytes, neutrophils, polymorphonucleated) respond to a chemical stimulus (when stimulated by substances called chemokines) by migrating along the concentration gradient of the stimulating agent, through a process called chemotaxis. The main known stimulating agents or chemokines are represented by the breakdown products of complement C5a, some N-formyl peptides generated from lysis of the bacterial surface or peptides of synthetic origin, such as formyl-methionyl-leucyl-phenylalanine (f-MLP) and mainly by a variety of cytokines, including Interleukin-8 (IL-8). Interleukin-8 is an endogenous chemotactic factor produced by most nucleated cells such as fibroblasts, macrophages, endothelial and epithelial cells subjected to the TNF-$\alpha$ (Tumor Necrosis Factor) stimulus, interleukins IL-1 $\alpha$ and IL-1 $\beta$ and bacterial wall lipopolysaccharides (LPS), as well as the same neutrophils exposed to the action of LPS or N-formyl peptides of bacterial origin (f-MLP). Belonging to the family of this chemotactic factor [also known as neutrophil activating factor (NAF), T-lymphocyte chemotactic factor, monocyte derived neutrophils chemotactic factor (MDNCF)] is a series of IL-8-like chemokines [GRO $\alpha$, $\beta$, $\gamma$ and NAP-2], which bind to the IL-8 receptors (Chang et al., J. Immunol., 148, 451, 1992). Neutrophils are the first line of defense against bacterial infection, owing to the ability of these cells to migrate from the peripheral blood through the endothelial junctions and the tissue matrices towards the action sites (i.e. along chemotactic factor concentration gradients) where they act by attacking the microorganisms, removing damaged cells and repairing tissues (M. A. Goucerot-Podicalo et al., Pathol. Biol (Paris), 44, 36, 1996).

In some pathological conditions, marked by exacerbated recruitment of neutrophils, a more severe tissue damage at the site is associated with the infiltration of neutrophilic cells. Recently, the role of neutrophilic activation in the determination of damage associated with post ischemia reperfusion and pulmonary hyperoxia was widely demonstrated. Experimental models [N. Sekido et al., Nature, 365, 654, 1993 and T. Matsumoto et al., Lab. Investig., 77, 119, 1997] and clinical studies [A Mazzone et al., Recent Prog. Med., 85, 397, 1994; G. Receipts et al., Atheroscl., 91, 1, 1991] have shown the direct correlation between cellular damage and the extent of PMN leukocyte infiltration, 18 being the most specific and powerful activator thereof. In patients affected by acute respiratory insufficiency (ARDS), the exacerbated recruitment of neutrophils in the airways and in pulmonary fluids can be closely correlated with the concentration of the cytokine IL-8 (E. J. Miller et al., Am. Rev. Respir. Dis., 146, 437, 1992) and with the severity of the pathology (Kurodowska et al., Immunol., 157, 2699, 1996). Treatment with anti-IL-8 antibody was shown to be effective in models of acute respiratory insufficiency and pulmonary damage caused by endotoxemia (K. Yokoi et al.; Lab. invest., 76, 375, 1997).

The specific role of IL-8 in causing damage following post ischemia reperfusion in patients affected by acute myocardium infarction was shown (Y. Abe et al., Br. Heart J., 70, 132, 1993); the key role exerted by IL-8 in the mediation of the damage associated with the post ischemia reperfusion is corroborated also by the results obtained using the anti-IL-8 antibody in an experimental model of focal cerebral ischemia in rabbits (T. Matsumoto et al., Lab. invest., 77, 119, 1997).

The biological activity of IL-8 is mediated by the interaction of the interleukin with CXCR1 and CXCR2 membrane receptors which belong to the family of seven transmembrane receptors, expressed on the surface of human neutrophils and of certain types of T-cells (L. Xu et al., J. Leukocyte Biol., 57, 335, 1995).

Although CXCR1 activation is known to play a crucial role in IL-8-mediated chemotaxis, it has been recently supposed that CXCR2 activation could play a pathophysiological role in cronic inflammatory diseases such as psoriasis. In fact, the pathophysiological role of IL-8 in psoriasis is also supported by the effects of IL-8 on keratinocyte functions. Indeed, IL-8 has been shown to be a potent stimulator of epidermal cell proliferation as well as angiogenesis, both important aspects of psoriatic pathogenesis (A. Tuschil et al. J Invest Dermatol, 99, 294, 1992; Koch A E et al, Science, 258, 1798, 1992). Additionally, IL-8 induced the expression of the major histocompatibility complex II (MHC-II) moiety HLA-DR on cultured keratinocytes (L. Kemeny et al., Int Arch Allergy Immunol, 10, 351, 1995). The effect of CXCL8 on keratinocyte function is supposed to be mediated by CXCR2 activation. In agreement with this hypothesis, it was reported that CXCR2 is overexpressed in epidermal lesional skin of psoriatic patients (R. Kulke et al., J. Invest. Dermatol., 110, 90, 1998).

In addition, there is accumulating evidence that the pathophysiological role of IL 8 in melanoma progression and metastasis could be mediated by CXCR2 activation.

The potential pathogenetic role of IL-8 in cutaneous melanoma is independent on its chemotactic activity on human PMNs. In fact, IL-8 is supposed to act as an autocrine growth and metastatic factor for melanoma cells.

Consistent amount of CXL8 have been found to be produced by melanoma cells and melanoma tumor cells are known to express immuneractive CXCR2 receptor (L. R. Bryan et al., Am J Surg, 174, 507, 1997). IL-8 is known to induce haptotactic migration as well as proliferation of melanoma cells (J. M. Wang et al., Biochem Biophys Res Commun, 169, 165, 1990).

Potential pathogenic role of IL-8 in pulmonary deseases (lung injury, acute respiratory distress syndrome, asthma, chronic lung inflammation, and cystic fibrosis) and, specifically, in the pathogenesis of COPD (chronic obstructive pulmonary disease) through the CXCR2 receptor pathway has been widely described (D. W P Hay and H. M. Sarau., Current Opinion in Pharmacology 2001, 1:242-247).

Phenylureido compounds have been described, which can selectively antagonize the binding of IL-8 to the CXCR2 receptor (J. R. White et al., J. Biol. Chem., 273, 10095, 1998); the use of these compounds in the treatment of pathological states mediated by Interleukin-8 is claimed in WO 98/07418.

Studies on the contribution of single (S) and (R) enantiomers of ketoprofen to the anti-inflammatory activity of the racemate and on their role in the modulation of the chemokine have demonstrated (P. Ghezzi et al., J. Exp. Pharm. Ther., 287, 969, 1998) that the two enantiomers and their salts with chiral and non-chiral organic bases can inhibit in a dose-dependent way the chemotaxis and increase in intracellular concentration of $Ca^{2+}$ ions induced by IL-8 on human PMN leukocytes (U.S. Pat. No. 6,069,172). It has been subsequently demonstrated (C. Bizzarri et al., Biochem. Pharmacol. 61, 1429, 2001) that Ketoprofen shares the inhibition activity of the biological activity of IL-8 with other molecules belonging to the class of non-steroidal anti-inflammatory (NSAIDs) such as flurbiprofen, ibuprofen and indomethacin. The cyclo-oxygenase enzyme (COX) inhibition activity typical of NSAIDs limits the therapeutical application of these compounds in the context of the treatment of neutrophil-dependent pathological states and inflammatory conditions such as psoriasis, idiopathic pulmonary fibrosis, acute respiratory failure, damages from reperfusion and glomerulonephritis. The inhibition of prostaglandin synthesis deriving from the action on cyclooxygenase enzymes involves the increase of the cytokine production which, like TNF-α, play a role in amplifying the undesired pro-inflammatory effects of neutrophils.

The lower COX inhibitory potency of the (R) enantiomers of NSAIDs belonging to the subclass of phenylpropionic acids, compared to the potency of the (S) enantiomers, has suggested that the (R) enantiomers of ketoprofen, flurbiprofen and ibuprofen might be potentially useful agents in the therapy of neutrophil-dependent pathologies. The fact that some (R) enantiomers are converted in vivo into the corresponding (S) enantiomers in several animals species and in humans, thus recovering COX inhibitory activity, is a severe limit to the use of these compounds in the therapy of IL-8 mediated pathologies.

The outlined premises account for the hard difficulties which have been met so far in the identification of selective IL-8 inhibitors belonging to the class of 2-phenylpropionic acids. It has been proposed that chiral inversion of R enantiomers of 2-phenylpropionic acids is due to the stereospecific formation of the intermediates R-profenyl-CoA thioesters; it has been demostrated hence that the carboxylic function derivatisation allows to avoid the "in vivo" metabolic inversion without affecting the IL-8 inhibition efficacy.

Structure Activity Relationship studies performed in the class of 2-phenylpropionic acid derivatives led to the identification of novel classes of potent and selective inhibitors of IL-8 biological activities suitable for "in vivo" administration. R-2-arylpropionic acid amides and N-acylsulfonamides have been described as effective inhibitors of IL-8 induced neutrophils chemotaxis and degranulation (WO 01/58852; WO 00/24710).

DETAILED DESCRIPTION OF THE INVENTION

We have now found out that selected subclasses of 2-arylpropionic acids show the surprising ability to effectively inhibit IL-8 induced neutrophils chemotaxis and degranulation without any evident effect on the cyclooxygenases activity.

Both the R and the S enantiomer of the (R,S)-2-aryl-propionic acids described herebelow are in fact inactive in the inhibition of cyclooxygenases in a concentration range between $10^{-5}$ and $10^{-6}$ M.

The present invention thus provides (R,S)-2-aryl-propionic acids of formula (I) and their single (R) and (S) enantiomers:

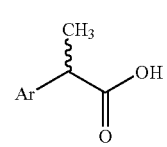

(I)

and pharmaceutically acceptable salts thereof,
wherein
Ar is a phenyl ring substituted by
    a group in the 3 (meta) position selected from a linear or branched $C_1$-$C_5$ alkyl, $C_2$-$C_5$-alkenyl or $C_2$-$C_5$-alkynyl group optionally substituted by $C_1$-$C_5$-alkoxycarbonyl, substituted or not-substituted phenyl, linear or branched $C_1$-$C_5$ hydroxyalkyl, aryl-hydroxymethyl, or the 3 (meta) linear or branched $C_1$-$C_5$ alkyl group forms, together with a substituent in ortho or para position and the benzene ring, saturated or unsaturated, substituted or non-substituted bicyclo aryls; or
    a group in the 4 (para) position selected from $C_1$-$C_5$-acyloxy, substituted or not-substituted benzoyloxy, $C_1$-$C_5$-acylamino, substituted or not-substituted benzoylamino, $C_1$-$C_5$-sulfonyloxy, substituted or not-substituted benzenesulfonyloxy, $C_1$-$C_5$-alkanesulfonylamino, substituted or not-substituted benzenesulfonylamino, $C_1$-$C_5$-alkanesulfonylmethyl, substituted or not-substituted benzenesulfonylmethyl, $C_3$-$C_6$-cycloalkyl; 2-furyl; 3-tetrahydrofuryl; 2 thiophenyl; 2-tetrahydrothiophenyl groups or a $C_1$-$C_8$ (alkanoyl, cycloalkanoyl, arylalkanoyl)-$C_1$-$C_5$-alkylamino, e.g. acetyl-N-methyl-amino, pivaloyl-N-ethyl-amino group; or
    a group in the 2 (ortho) position selected from substituted or not substituted arylmethyl, substituted or not substituted aryloxy, substituted or not substituted arylamino, wherein the substituents of the aryl group are selected from $C_1$-$C_4$ alkyl, $C_1$-$C_4$-alkoxy, chlorine, fluorine and/or trifluoromethyl groups;
for use as inhibitors of IL-8 induced human PMNs chemotaxis.

The phenyl ring in the Ar group may be optionally substituted with further groups such as $C_1$-$C_5$-alkyl or a halogen group.

The term "substituted" in the above definition means substituted with a group selected from $C_1$-$C_5$-alkyl, halogen, hydroxy, $C_1$-$C_5$-alkoxy, amino, $C_1$-$C_5$-alkylamino, nitro, or a cyano group.

Preferred Ar in compounds of formula (I) are phenyl groups 3-substituted by: isoprop-1-en-1-yl, ethyl, isopropyl, pent-2-en-3-yl, pent-3-yl, 1-phenyl-ethylen-1-yl, α-methyl-benzyl, α-hydroxybenzyl, α-hydroxyethyl, α-hydroxypropyl, bicyclic aryl structures such as 3-methyl-indan-5-yl, 3-methyl-indan-7-yl, 8-methyl-tetrahydronaphth-2-yl, 5-methyl-tetrahydronaphth-1-yl, and phenyl groups 4-substituted by trifluoromethanesulfonyloxy, 2-propanesulfonyloxy, benzylsulfonyloxy, benzenesulfonyloxy, 2'-ethylbenzenesulfonyloxy, 2'-chlorobenzenesulfonyloxy, methanesulfonylamino, trifluoromethanesulfonylamino, 2-propanesulfonylamino, benzylsulfonylamino, benzenesulfonylamino, 2'-ethylbenzenesulfonylamino, aminosulfonylmethyl, 2'-chlorobenzenesulfonylamino, trifluoromethanesulfonylmethyl, benzenesulfonylmethyl, aminosulfonyloxy, aminosulfonylamino; and phenyl groups 2-substituted by 2-(2,6-dichloro-phenylamino)-phenyl, 2-(2, 6-dichloro-phenyl-amino)-5-chloro-phenyl, 2-(2,6-dichloro-3-methyl-phenyl-amino)-phenyl, 2-(3-trifluoromethyl-phenyl-amino)-phenyl, 2-(2,6-dichloro-phenoxy)-phenyl, 2-(2-chloro-phenoxy)-phenyl, 2-(2,6-dichloro-benzyl)-phenyl, 2-(2-chloro-benzyl)-phenyl.

Particularly preferred Compounds of the invention are:
(R,S) 2-[3'-(alpha-ethyl-propyl)phenyl]propionic acid
(R) 2-[3'-(alpha-ethyl-propyl)phenyl]propionic acid
(S) 2-[3'-(alpha-ethyl-propyl)phenyl]propionic acid
2-[3'-(alpha-hydroxy-ethyl)phenyl]propionic acid, and the single diastereoisomers thereof
2-[3'-(alpha-hydroxy-propyl)phenyl]propionic acid and the single diastereoisomers thereof
(R,S) 2-[3'-isopropylphenyl]propionic acid
(R) 2-[3'-isopropylphenyl]propionic acid
(S) 2-[3'-isopropylphenyl]propionic acid
(R) 2-(4'-trifluoromethanesulfonyloxy)phenylpropionic acid
(S) 2-(4'-trifluoromethanesulfonyloxy)phenylpropionic acid
(R) 2-(4'-benzenesulfonyloxy)phenylpropionic acid
(S) 2-(4'-benzenesulfonyloxy)phenylpropionic acid
(R) 2-[4'-(2"-ethyl)benzenesulfonyloxy]phenylpropionic acid
(S) 2-[4'-(2"-ethyl)benzenesulfonyloxy]phenylpropionic acid
(R) 2-[4'-(2"-chloro)phenylsulfonyloxy]phenylpropionic acid
(S) 2-[4'(2"-chloro)phenylsulfonyloxy]phenylpropionic acid
(R) 2-[4'-(2"-propane)sulfonyloxy]phenylpropionic acid
(S) 2-[4'-(2"-propane)sulfonyloxy]phenylpropionic acid
(R) 2-(4'-benzylsulfonyloxy)phenylpropionic acid
(S) 2-(4'-benzylsulfonyloxy)phenylpropionic acid
(R) 2-(4'-aminosulfonyloxy)phenylpropionic acid
(S) 2-(4'-aminosulfonyloxy)phenylpropionic acid
(R) 2-(4'-trifluoromethanesulfonylamino)phenylpropionic acid
(S) 2-(4'-trifluoromethanesulfonylamino)phenylpropionic acid
(R) 2-(4'-methanesulfonylamino)phenylpropionic acid
(S) 2-(4'-methanesulfonylamino)phenylpropionic acid
(R) 2-[4'-(2"-propane)sulfonylamino]phenylpropionic acid
(S) 2-[4'-(2"-propane)sulfonylamino]phenylpropionic acid
(R) 2-(4'-benzenesulfonylamino)phenylpropionic acid
(S) 2-(4'-benzenesulfonylamino)phenylpropionic acid
(R) 2-[4'-(2"-ethyl)benzenesulfonylamino]phenylpropionic acid
(S) 2-[4'-(2"-ethyl)benzenesulfonylamino]phenylpropionic acid
(R) 2-[4'-(2"-chloro)benzenesulfonylamino]phenylpropionic acid
(S) 2-[4'-(2"-chloro)benzenesulfonylamino]phenylpropionic acid
(R) 2-(4'-benzylsulfonylamino)phenylpropionic acid
(S) 2-(4'-benzylsulfonylamino)phenylpropionic acid
(R) 2-(4'-aminosulfonylamino)phenylpropionic acid
(S) 2-(4'-aminosulfonylamino)phenylpropionic acid
(R) 2-(4'-trifluoromethanesulfonylmethyl)phenylpropionic acid
(S) 2-(4'-trifluoromethanesulfonylmethyl)phenylpropionic acid
(R) 2-(4'-benzenesulfonylmethyl)phenylpropionic acid
(S) 2-(4'-benzenesulfonylmethyl)phenylpropionic acid It is a further object of the present invention to provide novel compounds of formula (Ia)

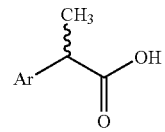

(Ia)

their single (R) and (S) enantiomers and pharmaceutically acceptable salts thereof,
wherein Ar is a phenyl ring substituted in the 4 (para) position with a group selected from $C_1$-$C_5$-sulfonyloxy, substituted or not-substituted benzenesulfonyloxy, $C_1$-$C_5$-alkanesulfonylamino, substituted or not-substituted benzenesulfonylamino, $C_1$-$C_5$-alkanesulfonylmethyl, substituted or not-substituted benzenesulfonylmethyl.

The phenyl ring in the Ar group of formula (Ia) may be optionally substituted with further groups such as $C_1$-$C_5$-alkyl or a halogen group.

The term "substituted" in the above definition means substituted with a group selected from $C_1$-$C_5$-alkyl, halogen, hydroxy, $C_1$-$C_5$-alkoxy, amino, $C_1$-$C_5$-alkylamino, nitro, or a cyano group.

Particularly preferred Compounds of Formula Ia as hereinbefore defined are:
(R) 2-(4'-trifluoromethanesulfonyloxy)phenylpropionic acid
(S) 2-(4'-trifluoromethanesulfonyloxy)phenylpropionic acid
(R) 2-(4'-benzenesulfonyloxy)phenylpropionic acid
(S) 2-(4'-benzenesulfonyloxy)phenylpropionic acid
(R) 2-[4'-(2"-ethyl)benzenesulfonyloxy]phenylpropionic acid
(S) 2-[4'-(2"-ethyl)benzenesulfonyloxy]phenylpropionic acid
(R) 2-[4'-(2"-chloro)phenylsulfonyloxy]phenylpropionic acid
(S) 2-[4'(2"-chloro)phenylsulfonyloxy]phenylpropionic acid
(R) 2-[4'-(2"-propane)sulfonyloxy]phenylpropionic acid
(S) 2-[4'-(2"-propane)sulfonyloxy]phenylpropionic acid
(R) 2-(4'-benzylsulfonyloxy)phenylpropionic acid
(S) 2-(4'-benzylsulfonyloxy)phenylpropionic acid
(R) 2-(4'-aminosulfonyloxy)phenylpropionic acid
(S) 2-(4'-aminosulfonyloxy)phenylpropionic acid
(R) 2-(4'-trifluoromethanesulfonylamino)phenylpropionic acid
(S) 2-(4'-trifluoromethanesulfonylamino)phenylpropionic acid
(R) 2-(4'-methanesulfonylamino)phenylpropionic acid
(S) 2-(4'-methanesulfonylamino)phenylpropionic acid
(R) 2-[4'-(2"-propane)sulfonylamino]phenylpropionic acid
(S) 2-[4'-(2"-propane)sulfonylamino]phenylpropionic acid
(R) 2-(4'-benzenesulfonylamino)phenylpropionic acid
(S) 2-(4'-benzenesulfonylamino)phenylpropionic acid
(R) 2-[4'-(2"-ethyl)benzenesulfonylamino]phenylpropionic acid
(S) 2-[4'-(2"-ethyl)benzenesulfonylamino]phenylpropionic acid
(R) 2-[4'-(2"-chloro)benzenesulfonylamino]phenylpropionic acid
(S) 2-[4'-(2"-chloro)benzenesulfonylamino]phenylpropionic acid
(R) 2-(4'-benzylsulfonylamino)phenylpropionic acid
(S) 2-(4'-benzylsulfonylamino)phenylpropionic acid
(R) 2-(4'-aminosulfonylamino)phenylpropionic acid
(S) 2-(4'-aminosulfonylamino)phenylpropionic acid
(R) 2-(4'-trifluoromethanesulfonylmethyl)phenylpropionic acid (S) 2-(4'-trifluoromethanesulfonylmethyl)phenylpropionic acid
(R) 2-(4'-benzenesulfonylmethyl)phenylpropionic acid
(S) 2-(4'-benzenesulfonylmethyl)phenylpropionic acid.

The compounds of the invention do not interfere with the production of $PGE_2$ in murine macrophages stimulated with lipopolysaccharides (LPS, 1 μg/ml) over concentration range: $10^{-5}$ to $10^{-6}$ M and are thus devoid of any inhibitory activity on cyclooxygenases (COX). Due to the absence of COX inhibitory activity in both the R and S enantiomers of the described 2-phenylpropionic acids, the compounds of the invention represent the first example of 2-phenylpropionic acids with the necessary features for a therapeutical use in pathologies related to the exacerbated neutrophil chemotaxis and activation induced by IL-8. The expected metabolic chiral inversion of the R-enantiomers of the present invention yields the corresponding S-enantiomers that share with the R enantiomers comparable characteristics in terms of IL-8 potency and COX selectivity.

The compounds of the invention of formula (I) are generally isolated in the form of their addition salts with both organic and inorganic pharmaceutically acceptable bases. Examples of such bases are: sodium hydroxide, potassium hydroxide, calcium hydroxide, (D,L)-Lysine, L-Lysine, tromethamine.

The 3 (meta) and 2 (ortho) substituted 2-arylpropionic acids of formula (I) and their enantiomers are described in WO 01/58852 and in WO 00/24710

(I)

Acids of formula I as defined above, are obtained by alkylation with stannanes of a polysubstituted 2-phenyl-propionic acid bearing a perfluorobutanesolfonate group in the ortho- or meta- or para-position, as described herein below.

The single enantiomers of 2-arylpropionic acids of formula (I) can be prepared by a total and stereospecific synthesis: the transformation is also known of racemates into one of the single enantiomers after transformation into 2-aryl-2-propyl-ketenes as described by Larse R D et al., J. Am. Chem. Soc., 111, 7650, 1989 and Myers A G, ibidem, 119, 6496, 1997. The stereoselective syntheses of 2-arylpropionic acids mainly relates to the S enantiomers, but they can be modified in order to obtain the R enantiomers through a convenient selection of the chiral auxiliary agent. For the use of arylalkylketones as substrates for the synthesis of α-arylalkanoic acids see e.g. B M Trost and J H Rigby, J. Org. Chem., 14, 2926, 1978; for arylation of Meldrum acids see J T Piney and R A Rowe, Tet. Lett., 21, 965, 1980; the use of tartaric acid as chiral auxiliary agent see Castaldi et al., J. Org. Chem., 52, 3019, 1987; for the use of a-hydroxy-esters as chiral reactants, see R D Larsen et al., J. Am. Chem. Soc., 111, 7650, 1989 and U.S. Pat. No. 4,940,813 cited here.

A process for the preparation 2-(2-OH-phenyl)-propionic acids and their esters is described in Italian Patent 1,283,649. An established and efficient method for the preparation of the R enantiomer of (R,S)-2-(5-benzoyl-2-acetoxy)-propionic acid and of the acids of formula (Ia) is the conversion of chlorides of said carboxylic acids into the corresponding prop-1-ketenes by reaction with a tertiary amine e.g. dimethyl-ethyl-amine, followed by the reaction of the ketene with R(−)pantolactone to yield the esters of R-enantiomers of said acids with R-dihydro-3-hydroxy-4,4-dimethyl-2(3H)furan-2-one. The subsequent saponification of the ester with LiOH provides the corresponding free acids.

A general process for the preparation of R-2-arylpropionic acids of formula (Ia) involves, for example, reaction of 4-hydroxy-phenylpropionic acids esters or 4-aminophenylpropionic acids esters with corresponding $C_1$-$C_5$-sulphonylchlorides or benzenesulphonylchlorides in presence of a suitable organic or inorganic base; or reaction of 4-chloromethylphenylpropionic acids esters with corresponding $C_1$-$C_5$-thiolates or benzenethiolates in presence of a suitable organic or inorganic base as described in detail in the section "General procedure for the synthesis of (S) and (R)-2-[(4'-aryl/alkyl-sulfonylamino)phenyl]propionic acids of formula Ia" and following sections. A typical preparation of compounds of formula (Ia) involves the reaction of hydroxyarylketones of formula (IIa) mono or polysubstituted by perfluorobutanesulfonylfluoride to yield perfluorobutanesulfonic esters of formula (IIb) where n is an integer from 1 to 9:

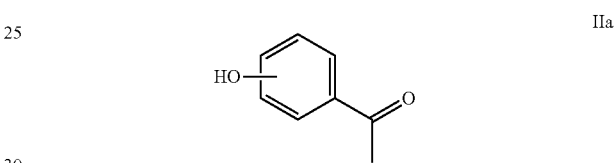
IIa

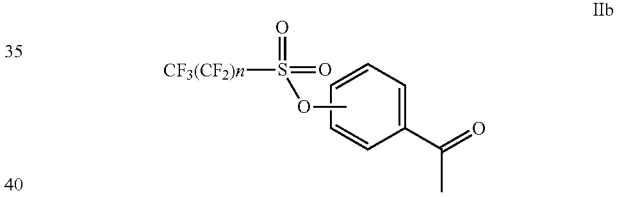
IIb

The compounds of formula (IIb) are subjected to Willgerodt rearrangement in order to obtain, after esterification and methylation on the alpha carbon, arylpropionic derivatives of formula (IIc) wherein n is an integer from 1 to 9 and $R_3$ represents a $C_1$-$C_4$ alkyl or $C_2$-$C_4$-alkenyl.

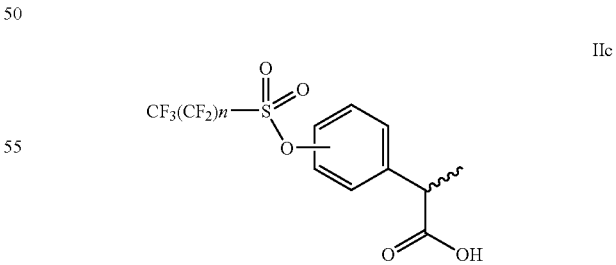
IIc

The compounds of formula (IIc) are reacted with the appropriate tributylstannane of formula $Bu_3SnR_4$ where R4 is a linear or branched $C_2$-$C_6$ alkyl; linear or branched $C_2$-$C_6$ alkenyl or linear or branched $C_2$-$C_6$ alkynyl, non-substituted or substituted with an aryl group, to obtain corresponding (R,S)-2-arylpropionates of formula (IId).

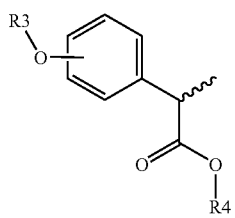

IId

The alkenyl or alkynyl groups can be hydrogenated in conditions of catalytic hydrogenation in order to obtain the correspondents saturated alkyl groups. The compounds of formula (IId) are subjected to the process of de-racemization as described above for conversion of the corresponding acid chlorides into ketenes that, by reaction with R(−)pantonolactone and subsequent hydrolysis, are converted into the pure R enantiomers; the reaction of the ketene intermediate with the chiral auxiliary S(+)-pantonolactone yields the corresponding pure S enantiomer.

The compounds of the invention of formula (I) were evaluated in vitro for their ability to inhibit chemotaxis of polymorphonucleate leukocytes (hereinafter referred to as PMNs) and monocytes induced by the fractions of IL-8 and GRO-α. For this purpose, in order to isolate the PMNs from heparinized human blood, taken from healthy adult volunteers, mononucleates were removed by means of sedimentation on dextran (according to the procedure disclosed by W. J. Ming et al., J. Immunol., 138, 1469, 1987) and red blood cells by a hypotonic solution. The cell vitality was calculated by exclusion with Trypan blue, whilst the ratio of the circulating polymorphonucleates was estimated on the cytocentrifugate after staining with Diff Quick.

Human recombinant IL-8 (Pepro Tech) was used as stimulating agents in the chemotaxis experiments, giving practically identical results: the lyophilized protein was dissolved in a volume of HBSS containing 0.2% bovin serum albumin (BSA) so thus to obtain a stock solution having a concentration of $10^{-5}$ M to be diluted in HBSS to a concentration of $10^{-9}$ M, for the chemotaxis assays.

During the chemotaxis assay (according to W. Falket et al., J. Immunol. Methods, 33, 239, 1980) PVP-free filters with a porosity of 5 μm and microchambers suitable for replication were used.

The compounds of the invention in formula (I) were evaluated at a concentration ranging between $10^{-6}$ and $10^{-10}$ M; for this purpose they were added, at the same concentration, both to the lower pores and the upper pores of the microchamber. Evaluation of the ability of the compounds of the invention of formula (I) to inhibit IL-8-induced chemotaxis of human monocytes was carried out according to the method disclosed by Van Damme J. et al. (Eur. J. Immunol., 19, 2367, 1989).

By way of example, inhibition data ($C=10^{-6}$ M) of some representative compounds in the IL-8 induced PMN chemotaxis test are reported in the following table:

| Example | Name | % inhibition ($C = 10^{-6}$ M) |
|---|---|---|
| 5 | (R,S) 2-[3'-isopropylphenyl]propionic acid | 51 ± 12 |
| 10 | (R) 2-[3'-isopropylphenyl]propionic acid | 43 ± 18 |
| 14 | (S) 2-[3'-isopropylphenyl]propionic acid | 50 ± 9 |
| 7 | (R,S), (R,S) 2-[3'-(alpha-methyl-benzyl)-phenyl]propionic acid | 54 ± 4 |

-continued

| Example | Name | % inhibition ($C = 10^{-6}$ M) |
|---|---|---|
| 16 | (R,S), (R,S) 2-[3'-(alpha-hydroxy-ethyl)-phenyl]propionc acid | 57 ± 6 |
| 18 | (R,S) 2-[(2'-(2'',6''-dichlorophenyl)-amino]phenyl propionic acid | 52 ± 3 |
| 19 | (R) 2-[(2'-(2'',6''-dichlorophenyl)-amino]phenyl propionic acid | 46 ± 14 |
| 20 | (S) 2-[(2'-(2'',6''-dichlorophenyl)-amino]phenyl propionic acid | 50 ± 7 |
| 6 | (R,S) 2-[3'-(alpha-ethyl-propyl)phenyl]-propionic acid | 58 ± 2 |
| 25 | (R,S) 2-[(2'-(2'',6''-dichloro)phenoxy)phenyl]propionic acid | 41 ± 9 |

The above listed compounds have shown a moderate potency in the GRO-α induced PMNs chemotaxis test suggesting a selective effect on the CXCR1 mediated pathway.

Particularly preferred compounds of the invention are compounds of Formula Ia, which show the additional property to effectively inhibit the GROA induced PMN chemotaxis; this activity allows the therapeutical use of these compounds in IL-8 related pathologies where the CXCR2 pathway is involved specifically or in conjunction with the CXCR1 signalling.

In the table below, biological activities of compounds showing high potency in the inhibition of PMN chemotaxis induced as by IL-8 as by the selective CXCR2 agonist GRO-α are reported.

Some examples of selective GRO-α potent inhibitors are included.

The dual inhibitors of the IL-8 and GRO-α induced biological activities are strongly preferred in view of the therapeutical applications of interest, but the described compounds selectively acting on CXCR1 IL-8 receptor or CXCR2 GRO-α/IL-8 receptor can find useful therapeutical applications in the management of specific pathologies as below described.

| Biological activity data on CXCR1 and CXCR2 receptors (% of inhibition) | | |
|---|---|---|
| Example | Name | IL-8 ($c = 10^{-8}$ M) | GRO-α ($c = 10^{-8}$ M) |
| 27 | (R) 2-(4'-benzenesulfonyl-amino)phenylpropionic acid | 49 ± 11 | 33 ± 11+ |
| 28 | (R) 2-(4'-methanesulfonyl-amino)phenylpropionic acid | 25 ± 7 | 32 ± 5 |
| 29 | (R) 2-[4'-(2''-propane)sulfonyl-amino]phenylpropionic acid | 54 ± 14 | 44 ± 12 |
| 30 | (R) 2-(4'-trifluoromethanesulfonylamino)phenylpropionic acid | 8 ± 10 | 40 ± 14 |
| 31 | (R) 2-(4'-benzylsulfonyl-amino)phenylpropionic acid | 60 ± 10 | 24 ± 8 |
| 32 | (R) 2-[4'-(2''-chloro)benzenesulfonylamino]phenylpropionic acid | −2 ± 10 | 66 ± 10 |
| 33 | (R) 2-[4'-(2''-ethyl)benzenesulfonylamino]phenylpropionic acid | 44 ± 14 | 80 ± 10 |
| 34 | (R) 2-(4'-aminosulfonyl-amino)phenylpropionic acid | 55 ± 10 | 2 ± 5 |
| 35 | (R) 2-(4'-benzenesulfonyl-oxy)phenylpropionic acid | 28 ± 11 | 25 ± 10 |
| 38 | (R) 2-[4'-(2''-propane)sulfonyl-oxy]phenylpropionic acid | 49 ± 8 | 46 ± 6 |

-continued

Biological activity data on CXCR1 and CXCR2 receptors
(% of inhibition)

| Example | Name | IL-8 (c = $10^{-8}$ M) | GRO-α (c = $10^{-8}$ M) |
|---|---|---|---|
| 37 | (R) 2-(4'-trifluoromethane-sulfonyloxy)phenylpropionic acid | 62 ± 7 | 59 ± 10 |
| 36 | (R) 2-(4'-benzylsulfonyl-oxy)phenylpropionic acid | 59 ± 11 | 25 ± 11 |
| 39 | (R) 2-[4'-(2''-chloro)benzenesul-fonyloxy]phenylpropionic acid | 25 ± 7 | 65 ± 10 |
| 40 | (R) 2-[4'-(2''-ethyl)benzenesul-fonyloxy]phenylpropionic acid | 45 ± 13 | 70 ± 10 |
| 41 | (R) 2-(4'-aminosulfonyloxy)-phenylpropionic acid | 65 ± 10 | 5 ± 7 |
| 43 | (R) 2-(4'-trifluoromethanesul-fonylmethyl)phenylpropionic acid | 48 ± 7 | 45 ± 7 |
| 42 | (R) 2-(4'-benzenesulfonyl-methyl)phenylpropionic acid | 60 ± 7 | 52 ± 5 |

All the compounds of the invention demonstrated a high degree of selectivity towards the inhibition of the IL-8 induced chemotaxis compared to the chemotaxis induced by C5a ($10^{-9}$ M) or f-MLP ($10^{-8}$ M).

The compounds of formula (I), evaluated ex vivo in the blood in toto according to the procedure disclosed by Patrignani et al., in J. Pharmacol. Exper. Ther., 271, 1705, 1994, were found to be totally ineffective as inhibitors of cyclooxygenase (COX) enzymes.

In almost all cases, the compounds of formula (I) do not interfere with the production of $PGE_2$ induced in murine macrophages by lipopolysaccharides stimulation (LPS, 1 μg/mL) at a concentration ranging between $10^{-5}$ and $10^{-7}$ M. Inhibition of the production of $PGE_2$ which may be recorded, is mostly at the limit of statistical significance, and more often is below 15-20% of the basal value. The reduced effectiveness in the inhibition of the CO constitutes an advantage for the therapeutical application of compounds of the invention in as much as the inhibition of prostaglandin synthesis constitutes a stimulus for the macrophage cells to amplify synthesis of TNF-α (induced by LPS or hydrogen peroxide) that is an important mediator of the neutrophilic activation and stimulus for the production of the cytokine Interleukin-8.

In view of the experimental evidence discussed above and of the role performed by Interleukin-8 (IL-8) and congenetics thereof in the processes that involve the activation and the infiltration of neutrophils, the compounds of the invention are particularly useful in the treatment of a disease such as psoriasis (R. J. Nicholoff et al., Am. J. Pathol., 138, 129, 1991). Further diseases which can be treated with the compounds of the present invention are intestinal chronic inflammatory pathologies such as ulcerative colitis (Y. R. Mahida et al., Clin. Sci., 82, 273, 1992) and melanoma, chronic obstructive pulmonary disease (COPD), bollous pemphigo, rheumatoid arthritis (M. Selz et al., J. Clin. Invest., 87, 463, 1981), idiopathic fibrosis (E. J. Miller, previously cited, and P. C. Carré et al., J. Clin. Invest., 88, 1882, 991), glomerulonephritis (T. Wada et al., J. Exp. Med., 180, 1135, 1994) and in the prevention and treatment of damages caused by ischemia and reperfusion.

Inhibitors of CXCR1 and CXCR2 activation find useful applications, as above detailed, particularly in treatment of chronic inflammatory pathologies (e.g. psoriasis) in which the activation of both IL-8 receptors is supposed to play a crucial pathophysiological role in the development of the disease.

In fact, activation of CXCR1 is known to be essential in IL-8-mediated PMN chemotaxis (Hammond M et al, J Immunol, 155, 1428, 1995). On the other hand, activation of CXCR2 activation is supposed to be essential in IL-8-mediated epidermal cell proliferation and angiogenesis of psoriatic patients (Kulke R et al., J Invest Dermatol, 110, 90, 1998).

In addition, CXCR2 selective antagonists find particularly useful therapeutic applications in the management of important pulmonary diseases like chronic obstructive pulmonary disease COPD (D. W P Hay and H. M. Sarau., Current Opinion in Pharmacology 2001, 1:242-247).

It is therefore a further object of the present invention to provide compounds for use in the treatment of psoriasis, ulcerative colitis, melanoma, chronic obstructive pulmonary disease (COPD), bollous pemphigo, rheumatoid arthritis, idiopathic fibrosis, glomerulonephritis and in the prevention and treatment of damages caused by ischemia and reperfusion, as well as the use of such compounds in the preparation of a medicament for the treatment of diseases as described above. Pharmaceutical compositions comprising a compound of the invention and a suitable carrier thereof, are also within the scope of the present invention. The compounds of the invention, together with a conventionally employed adjuvant, carrier, diluent or excipient may, in fact, be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the acids of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Liquid forms, including the injectable compositions described herebelow, are always stored in the absence of light, so as to avoid any catalytic effect of light, such as hydroperoxide or peroxide formation. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the acid derivative of formula I in such compositions is typically a minor component, frequently ranging between 0.05 to 10% by weight with the remainder being the injectable carrier and the like. The mean daily dosage will depend upon various factors, such as the seriousness of the disease and the conditions of the patient (age, sex and weight). The dose will generally vary from 1 mg or a few mg up to 1500 mg of the compounds of formula (I) per day, optionally divided into multiple administrations. Higher dosages may be administered also thanks to the low toxicity of the compounds of the invention over long periods of time. The above described components for orally administered or injectable compositions are merely representative. Further materials as well as processing techniques and the like are set out in Part 8 of "Remington's Pharmaceutical Sciences Handbook", $18^{th}$ Edition, 1990, Mack Publishing Company, Easton, Pa., which is incorporated herein by reference.

The compounds of the invention can also be administered in sustained release forms or from sustained release drug delivery systems. A description of representative sustained release materials can also be found in the incorporated materials in the Remington's Handbook as above.

The present invention shall be illustrated by means of the following examples which are not construed to be viewed as limiting the scope of the invention.

In the description of the compounds of the invention of formula (I), the convention has been adopted of indicating the absolute configurations of any chiral substituents that may be present in the substituent R' of said compounds with prime signs (e.g., R', S', S" etc.).

Abbreviations: THF: tetrahydrofuran; DMF: dimethylformamide; AcOEt: ethyl acetate, HOBZ: 1-hydroxybenzotriazol, DCC: dicyclohexylcarbodiimide.

Materials and Methods
General Method of Synthesis for 2-aryl-propionic acids of Formula I and R-enantiomers Thereof.

Under stirring, at r.t. and excluding humidity, 12.0 g of anhydrous $K_2CO_3$ (86.2 mmol) are added to a 80.0 mmol solution of (o,m,p)-hydroxyacetophenone (mono or polysubstituted on the phenyl) in acetone (80 ml). The mixture is stirred for 30' at r.t. Then a solution of perfluorobutansulfonylfluoride (15.5 ml 86.1 mmol) in acetone (30 ml) is dripadded and the mixture refluxed for 2 hours. After cooling at r.t. the solid is filtered and the filtrate evaporated to dryness. The residue is taken up in EtOAc (100 ml). The organic solution is washed with a saturated solution of $KHCO_3$ (20 ml) and then with a saturated solution of NaCl (20 ml). After drying on $Na_2SO_4$ and evaporation of the solvent the corresponding perflurobutansulfonylester is obtained under the form of an oil, sufficiently pure to be used in the following reaction and with practically quantitative yield.

A mixture of the acetophenone perflurobutansulfonyl ester so obtained (80.0 mmol), sulfur (2.95 g, 92.0 mmol) and morpholine (8.0 ml; 92.0 mmol) is refluxed for 6 hours. After cooling at r.t. the solution is poured onto a mixture of ice and 6N HCl (40 ml). It is extracted with $CH_2Cl_2$ (2×50 ml); the organic extracts are dried over $Na_2SO4$ and the solvent is evaporated to give a crude yellow oil that, after purification by means of chromatography on silica gel (eluent: n-hexane/EtOAc 9:1) gives the corresponding morpholinamide as a transparent oil (yield 73%).

A solution of morpholinamide (58.0 mmol) in glacial acetic acid (25.0 ml) is added to 37% HCl (40 ml) and then it is refluxed for 16 hours under stirring. After cooling at r.t., the mixture is filtered from the precipitate that separated out. After evaporation of the filtrate, the residue is diluted with $H_2O$ (50 ml) and extracted with EtOAc (2×50 ml). The combined organic extracts are washed with a saturated solution of NaCl (20 ml), dried over $Na_2SO_4$ and evaporated at reduced pressure to give an oil from which, by crystallization from n-hexane, provides an (o,m,p)perfluorbutanesulfonate of 2-phenyl-acetic acid in solid crystalline form (yield 90-93%/o). The subsequent esterification with concentrated $H_2SO_4$ in hot absolute ethanol supplies the corresponding ethyl ester in practically quantitative yield. In small successive portions, a 60% suspension of sodium hydride in mineral oil (for a total of 1.6 g; 66.7 mmol) is added to a solution of ethyl(o,m,p)-perfluorobutansulfonyloxy-2-phenyl-acetate (e.g. 25 mmol) in THF (50 ml) cooled to T=0.5° C. is added gradually. After 15' methyl iodide (1.88 ml; 30.2 mmol) is dripped in and left to react at r.t. for 3.5 h. The reaction is stopped by adding a saturated solution to of $NH_4Cl$ (45 ml); the solvent is evaporated at reduced pressure and the aqueous phase is extracted with $CH_2Cl_2$ (3×50 ml); the combined organic extracts are washed with a saturated solution of NaCl (200 ml), dried over $Na_2SO_4$ and evaporated at reduced pressure to give a residue that, after chromatographic purification, provides the ethyl ester of the corresponding (o,m,p) perfluorobutansulfonyloxy-2-phenyl-propionic acid as a solid (yield 70%).

Starting from the ethyl ester of ethyl(o,m,p)-(nonafluorobutansulfonyloxy)-2-phenylpropionate racemates are prepared of the 2-aryl-propionic acids of formula I by means of reacting said sulfonates with organostannanes following the methods described by Mitchell T. N., Synthesis, 803, 1992 and Ritter K., Synthesis, 735, 1993.

According to the method illustrated above the following compounds were prepared:

Example 1

2-[3'-(isopropenyl)phenyl]propionic acid

The acid was synthesized starting from ethyl 3'-perfluorobutansulfonyloxy-2-phenylpropionate (7.63 mmol) that was dissolved in N-ethylpirrolidone (30 ml); to the mixture is added anhydrous LiCl (0.94 g, 22.9 mmol), triphenylarsine (90 mg; 0.3 mmol) and dipalladiumtribenzylidenacetone (0.173 g; 0.15 mmol Pd). After 5' at r.t. tributylisopropenyltin (2.83 g; 8.55 mmol) is added and the solution is stirred for 5 h at T=90° C. After cooling the solution to r.t., the mixture is diluted with hexane and a saturated solution of KF is added; after filtration and separation of the phases the organic phase is dried over $Na_2SO_4$ and evaporated under vacuum. The purification of the residue by means of flash chromatography gives 2-[3'-isopropylphenyl]ethyl propionate. (Ritter K., Synthesis, 735, 1993 and Mitchell T. N., Synthesis, 803, 1992).

1N NaOH (5 ml) was added to a solution of the ester in dioxan (5 ml) and the solution is stirred at r.t. overnight. After evaporation of the organic solvent, the mixture is acidified to pH=2 with 2N HCl until complete precipitation of the product, which is isolated, as a white solid by filtration.

$^1$H-NMR (CDCl$_3$): δ 10.0 (bs, 1H, COOH); 7.28 (m, 1H); 7.15 (m, 1H); 7.05 (m, 2H); 5.02 (s, 2H); 3.75 (m, 1H); 2.34 (m, 1H); 1.8-1.6 (m, 4H); 1.45 (d, 3H, 1=7 Hz); 0.78 (s, 3H).

Example 2

2-[3'-(alpha-ethyl-propenyl)phenyl]propionic acid

According to the method reported above, the acid was synthesized by using as starting reagent tributyl-(α-ethyl) propenyl tin synthesized according to known methods (Ritter K., Synthesis, 735, 1993 and Mitchell T. N., Synthesis, 803, 1992).

$^1$H-NMR (CDCl$_3$): δ 10.0 (bs, 1H, COOH); 7.28 (m, 1H); 7.15 (m, 1H); 7.05 (m, 2H); 5.5 (m, 1H); 3.75 (m, 1H); 1.8-1.6 (q, 2H); 1.45 (d, 3H, J=7 Hz); 0.85 (d, 3H, J=7 Hz); 0.78 (t, 3H, J=7 Hz)

Example 3

3-[3'-(1''-styrenyl)phenyl]propionic acid

According to the method reported above, the acid was synthesized by using as starting reagent tributyl-α-styrenyl tin synthesized according to known methods (Ritter K., Synthesis, 735, 1993 and Mitchell T. N., Synthesis, 803, 1992).

$^1$H-NMR (CDCl$_3$): δ 11.0 (bs, 1H, COOH); 7.38-7.13 (m, 9H); 3.95 (m, 2H); 3.81 (m, 1H); 1.72 (d, 3H, J=7 Hz).

Example 4

2-[3'-isobutenyl-phenyl]propionic acid

According to the method reported above the acid was synthesized by using as starting reagent tributyl isobutenyl-tin synthesized according to methods (Ritter K., Synthesis, 735, 1993 and Mitchell T. N., Synthesis, 803, 1992).

$^1$H-NMR (CDCl$_3$): δ 10.0 (bs, 1H, COOH); 7.28 (m, 1H); 7.15 (m, 1H); 7.05 (m, 2H); 5.5 (m, 1H); 3.75 (m, 1H); 1.45 (d, 3H, J=7 Hz); 1.45 (s, 3H); 1.35 (s, 3H).

By way of example the preparation of 2-[(3'-isopropyl) phenyl]propionic acid is disclosed

Example 5

A mixture of 2-[3'-(isopropenyl)phenyl]ethyl propionate, obtained by the method reported above (1 g; 4.6 mmol), 95% ethyl alcohol (10 ml) and Pd/C 10% (100 mg) are subjected to catalytic hydrogenation at r.t. and atmospheric pressure until the initial reagent disappears (2 h). The catalyst is filtered off on Celite and, after evaporation of the filtrate, a transparent oil is obtained (0.99 g; 4.5 mmol) that is hydrolysed in a 1N solution of KOH in ethyl alcohol (10 ml) at T=80° C. for 2 h. After cooling at r.t. the solvents are evaporates at reduced pressure; the residue is taken up with EtOAc (20 ml) and it is extracted with H$_2$O (3×10 ml); the aqueous phase is acidified to pH=2 with 2N HCl and counter-extracted with EtOAc (2×10 ml); the organic extracts are combined and washed with a saturated solution of NaCl, are dried over Na2SO4 and evaporated at reduced pressure to give 2-[(3'-isopropyl)phenyl]propionic acid (0.75 g; 3.6 mmol)

$^1$H-NMR (CDCl$_3$): δ 10.5 (bs, 1H, COOH); 7.15-7.08 (m, 4H); 3.55 (m, 1H); 2.91 (m, 1H); 1.45 (d, 3H, J=7 Hz); 1.26 (d, 3H, J=7 Hz).

According to the same method the following compounds were prepared:

Example 6

(R,S) 2-[3'-(alpha-ethyl-propyl)phenyl]propionic acid $^1$H-NMR (CDCl$_3$): δ 10.0 (bs, 1H, COOH); 7.28 (m, 1H); 7.15 (m, 1H); 7.05 (m, 2H); 3.75 (m, 1H); 2.34 (m, 1H); 1.8-1.6 (m, 4H); 1.45 (d, 3H, J=7 Hz); 0.78 (t, 6H, J=7 Hz).

Example 7

(R,S) 3-[3'-(alpha-methyl)benzyl-phenyl]propionic acid $^1$H-NMR (CDCl$_3$): δ 11.0 (bs, 1H, COOH); 7.38-7.13 (m, 9H); 4.20 (m, 1H); 3.78 (m, 1H); 1.72 (d, 3H, J=7 Hz); 1.55 (d, 3H, J=7 Hz).

Example 8

(R,S) 2-[3'-isobutylphenyl]propionic acid $^1$H-NMR (CDCl$_3$): δ 10.0 (bs, 1H, COOH); 7.28 (m, 1H); 7.15 (m, 1H); 7.05 (m, 2H); 3.78 (m, 1H); 2.50 (d, 2H, J=7 Hz); 1.9 (m, 1H); 1.45 (d, 3H, J=7 Hz); 0.98 (d, 6H, J=7 Hz).

Example 9

(R,S) 2-[(3'-cyclohexylmethyl)phenyl]propionic acid

The acid was synthesized according to the procedure reported above, by using as starting reagents cyclohexylmethyl zinc bromide, commercial reactant and ethyl-3-perfluorobutansulfonyloxy-2-phenylpropionate.

$^1$H-NMR (CDCl$_3$): δ 10.15 (bs, 1H, COOH); 7.1 (s, 1H); 7.25-7.35 (m, 3H,); 3.75 (q, 1H, J$_1$=15 Hz, J$_2$=7 Hz); 2.48 (d, 2H, J=7 Hz); 1.77-1.70 (m, 4H); 1.60-1.45 (d, 3H, J=7 Hz+m, 1H); 1.30-1.10 (m, 4H); 1.08-0.90 (m, 2H).

Each of the racemates of the acids of formula φ-Ar$_b$—C(CH$_3$)H—CO$_2$H is then transformed into the R enantiomer through the stereospecific preparation of the corresponding ester with R-pantolactone (via ketene intermediate) operating according to the methods described by Myers A. G. et al., J. Am. Chem. Associates, 119, 6496, 1997 and by Larsen R. D. et al., J. Am. Chem. Associates, 111, 7650 1989.

In this way the following compounds were prepared

Example 10

(R)-2-[(3'-isopropyl)phenyl]-propionic acid

[α]$_D$=−23 (c=0.5; CH$_2$Cl$_2$)

$^1$H-NMR (CDCl$_3$): δ 10.0 (bs, 1H, COOH); 7.15-7.10 (m, 4H); 3.65 (m, 1H); 2.90 (m, 1H); 1.45 (d, 3H, J=7 Hz); 1.32 (d, 3H, J=7 Hz).

Example 11

(R)-2-[3'-(1''-ethyl-propyl)phenyl]propionic acid

[α]$_D$=−29 (c=0.5; CH$_2$Cl$_2$)

$^1$H-NMR (CDCl$_3$): δ 10.25 (bs, 1H, COOH); 7.28 (m, 1H); 7.15 (m, 1H); 7.05 (m, 2H); 3.75 (m, 1H); 2.34 (m, 1H); 1.8-1.6 (m, 4H); 1.45 (d, 3H, J=7 Hz); 0.78 (t, 6H, J=7 Hz).

Example 12

(R) 2-[3'-isobutylphenyl]propionic acid

[α]$_D$=−35 (c=0.5; CH$_2$Cl$_2$)

$^1$H-NMR (CDCl$_3$): δ 10.0 (bs, 1H, COOH); 7.28 (m, 1H); 7.15 (m, 1H); 7.05 (m, 2H); 3.78 (m, 1H); 2.50 (d, 2H, J=7 Hz); 1.9 (m, 1H); 1.45 (d, 3H, J=7 Hz); 0.98 (d, 6H, J=7 Hz)

Example 13

(R),(R'S')-3-[(3'-α-methyl)benzylphenyl]propionic acid

[α]$_D$=−49 (c=0.5; CH$_2$Cl$_2$)

$^1$H-NMR (CDCl$_3$): δ 11.0 (bs, 1H, COOH); 7.38-7.13 (m, 9H); 4.20 (m, 1H); 3.78 (m, 1H); 1.72 (d, 3H, J=7 Hz); 1.55 (d, 3H, J=7 Hz).

Following the same procedure above described but using S-pantolactone, the stereospecific preparation of the S enantiomers was achieved:

Example 14

(S)-2-[(3'-isopropyl)phenyl]-propionic acid

[α]$_D$=+24.2 (c=0.5; CH$_2$Cl$_2$)

$^1$H-NMR (CDCl$_3$): δ 10.1 (bs, 1H, COOH); 7.12-7.07 (m, 4H); 3.64 (m, 1H); 2.91 (m, 1H); 1.45 (d, 3H, J=7 Hz); 1.30 (d, 3H, J=7 Hz).

Example 15

(R),(R',S'))-2-[(3'-α-hydroxybenzyl)phenyl]propionic acid

To a solution of R(−)ketoprofen (0.254 g, 1 mmol) in ethyl alcohol (5 ml) triethylamine (0.12 g; 1 mmol) and a catalyst (d/C 5% 0.025 g) are added; the mixture is hydrogenated at r.t. and atmospheric pressure for 3 hours. After removal of the catalyst by filtration on a Celite cake, the filtrate is evaporated and the residue purified on a chromatographic column. The product is obtained as a white solid (yield 85%).

[α]$_D$=−45.7 (c=1; CHCl$_3$)

$^1$H-NMR (CDCl$_3$): δ 7.41-7.3 (m, 3H); 7.31-7.14 (m, 6H); 5.75 (s, 1H); 4.02 (bs, 1H, OH); 3.68 (q, 1H, J=7 Hz) 1.4 (d, 3H, J=7 Hz).

Following the same procedure described for the example 15 and starting from (R,S)-2-[(3'-acetyl)phenyl]-propionic acid, the following was obtained:

Example 16

(R,S), (R,S) 2-[3'-(alpha-hydroxy-ethyl)phenyl]propionic acid $^1$H-NMR (CDCl$_3$): δ 7.40-7.15 (m, 4H); 4.90 (q, 1H, J=7 Hz); 3.78 (q, 1H, J=7 Hz); 1.55 (m, 6H).

Example 17

(R),(R',S')-2-[3'-α,-hydroxy-α-methyl benzyl)phenyl]propionic acid

To a solution of the methyl ester of R(−)-ketoprofen (0.269, 1 g) in ethyl ether (10 ml) a 3.0 M solution of methylmagnesium bromide in ethyl ether (2 mmol) is added; the resulting solution is refluxed for 2 hours. After cooling of the mixture, the organic phase is washed with a 5% solution of NaH$_2$PO$_4$ (2×10 ml), dried over Na$_2$SO$_4$ and evaporated under vacuum. The residue obtained is redissolved in a 1:1 mixture of MeOH/1N NaOH (5 ml) and the solution stirred overnight. The organic solvent is removed under vacuum and the aqueous solution acidified to pH=2; the precipitate formed is filtered, washed with water. The (R),(R',S')-2-[3'-α-hydroxy-α-methylbenzyl)phenyl]propionic acid is obtained as a white powder.

[α]$_D$=−45.3 (c=1; CHCl$_3$)

$^1$H-NMR (CDCl$_3$): δ 7.41-7.3 (m, 3H); 7.31-7.14 (m, 6H); 4.02 (bs, 1H, OH); 3.68 (q, 1H, J=7 Hz); 1.4 (d, 3H, J=7 Hz).

Preparation of (R,S) 2-[2'-(2",6"-dichlorophenyl)aminophenyl propionic acid (Example 18), (R) 2-[2'-(2',6"-dichlorophenyl)aminophenyl propionic acid (Example 19) and (S) 2-[2'-(2",6"-dichlorophenyl)aminophenyl propionic acid (Example 20).

The compound was prepared as a racemic mixture in accordance with the method reported in Geigy, J R; Gb Patent 1.132.318 (30 Oct. 1968). The optical resolution to give examples 19 and 20 was performed by means of salification with R(+)-N-methylbenzylamine according to the method disclosed in Arzneim. Forsch. 19' 96, 46:9 891-894 by Akguen et al.

Example 21

Preparation of (R,S)-(2-(3'-benzyl)phenyl propionic acid
1. Methyl 2-bromophenylacetate To a solution of 2-bromophenyl acetic acid (2 g; 9.30 mmol) in methyl alcohol (10 ml) is added a catalytic amount of conc. H$_2$SO$_4$, (3 drops); the solvent is stirred at r.t. for 18 h. and is then evaporated. The residue oil is taken up with ethyl ether (10 ml); the organic phase is then washed with —H$_2$O (3×10 ml), dried over Na$_2$SO$_4$ and evaporated to give 2.12 g of methyl ester in the form of a transparent oil.

Yield: quantitative $^1$H-NMR (CDCl$_3$): δ 7.60 (d, 1H, J=7 Hz); 7.28-7.20 (m, 2H); 7.1-7.0 (m, 1H); 3.8 (s, 2H); 3.72 (s, 3H).

2. Methyl 2-(2')bromophenylpropionate

To a solution of diisopropylamine (1.66 ml; 11.8 mmol) in anhydrous THF (30 ml) maintained under stream of Ar and cooled to T=−10° C., is added, by dripping, a solution of n-butyllithium in n-hexane (1.6 M; 7.4 ml; 11.8 mmol); the addition is carried out in such way that the temperature does not exceed 0° C. On completion of the addition the mixture is stirred at T=−4° C. for 30 minutes, then methyl 2-bromophenyl acetate (1.9 g; 8.30 mmol) is added in anhydrous THF (8 ml). When the addition is finished, the mixture is stirred at r.t. for 1 h. Then the mixture is cooled again to T=−2° C. and methyl iodide (0.81 ml; 12.75 mmol) is added. The mixture is stirred at r.t. for 2 h until the starting product disappears; the ThF is evaporated to dryness, the residue is taken up in CHCl$_3$ (10 ml) and ml is washed with 1N HCl (3×10) and then with a saturated solution of NaCl (2×10 ml). It is acidified on Na$_2$SO$_4$ and evaporated at reduced pressure to give a dark red oily residue (1.95 g; 8.02 mmol) of sufficient purity to be used for the following stages.

Yield 96%

$^1$H-NMR (CDCl$_3$): δ 7.60 (d, 1H, J=7 Hz); 7.30-7.26 (m, 2H); 7.2-7.15 (m, 1H); 4.25 (q, 1H, J=7 Hz); 3.75 (s, 3H); 1.75 (d, 3H, J=7 Hz).

3. Methyl 2-(2'-)benzylphenylpropionate

Zinc powder (2.412 g; 36.9 mmol) is loaded into a flask under Ar. The flask is cooled off to T=0-4° C. with an ice/water bath and a solution of benzyl bromide (2.109 g; 12.3 mmol) in anhydrous TBF (10 ml) is added by means of slow dripping. The mixture is stirred at such temperature for 3 h until the starting product disappears. In parallel, in another flask under Ar tetrakis(triphenylphosfine)palladium (410 g; 0.35 mmol) and methyl 2-(2'-bromophenyl)propionate (1.9 g; 7.8 mmol) is loaded; the solution of organotin previously obtained is added and, when the dripping is finished, the solution is raised to reflux temperature for 18 h. After cooling at r.t. the mixture is diluted with 0.1N HCl (10 ml) and ethyl ether (15 ml) is added; they are shaken and the two phases are separated, the aqueous phase is again extracted with ethyl ether (3×15 ml); the organic extracts, combined, are washed with a saturated solution of $NaHCO_3$, dried over $Na_2SO_4$ and evaporated at reduced pressure to give a waxy residue that, after trituration with isopropyl ether overnight and filtration under vacuum, gives methyl 2-(2'-benzylphenyl)propionate in the form of a white solid (1.52 g; 6 mmol).

Yield 77%

$^1$H-NMR ($CDCl_3$): δ 7.50-7.25 (m, 5H); 7.24-7.15 (m, 2H); 7.10-7.05 (m, 2H); 4.25 (q, 1H, J=7 Hz); 4.15 (s, 2H); 3.75 (s, 3H); 1.55 (d, 3H, J=7 Hz).

4. (R,S) 2-(2'-Benzylphenyl)propionic acid

Methyl 2-(2'-benzylphenyl)propionate (1.5 g; 5.9 mmol) is dissolved in methyl alcohol (5 ml). 1M NaOH (7.1 ml) is added to the solution and the resulting solution is refluxed for 3 h; then it is stirred at r.t. for 18 h. The alcohol is then evaporated at reduced pressure and the residue is taken up with water; the aqueous phase is brought to pH=1 with 1N HCl and extracted with ethyl ether (3×5 ml). The combined organic extracts are washed with a saturated solution of $NaHCO_3$, dried over $Na_2SO_4$ and evaporated at reduced pressure to give (R,S) 2-(2'-benzylphenyl)propionic acid (1.06 g; 4.42 mmol) as a clear yellow oil.

Yield 75%

$^1$H-NMR ($CDCl_3$): δ 9.25 (bs, 1H, COOH); 7.55-7.35 (m, 5H); 7.24-7.15 (m, 2H); 7.10-7.05 (m, 2H); 4.25 (q, 1H, J=7 Hz); 4.15 (s, 2H); 1.50 (d, 3H, J=7 Hz).

According to the same method the following compounds were prepared

Example 22

(R,S) 2-[2'-[2"-chloro)benzyl]phenyl propionic acid $^1$H-NMR ($CDCl_3$): δ 10.0 (bs, 1H, COOH); 7.40-7.35 (m, 1H); 7.34-7.25 (m, 3H); 7.20-7.15 (m, 2H); 7.10-7.00 (m, 1H); 6.95-6.80 (m, 1H); 4.20 (q, 1H, J=7 Hz); 4.12 (s, 2H); 1.53 (d, 3H, J=7 Hz)

Example 23

(R,S) 2-[2'-(2",6"-dichloro)benzyl phenyl propionic acid $^1$H-NMR ($CDCl_3$): δ 9.55 (bs, 1H, COOH); 7.40-7.30 (d, 2H, J=8 Hz); 7.27-7.15 (m, 4H); 6.70-6.60 (d, 1H, J=8 Hz); 4.27 (s, 2H); 4.15 (q, 1H, J=7 Hz); 1.55 (d, 3H, J=7 Hz).

Example 24

Preparation of (R,S) 2-(2'-phenoxy)phenyl propionic acid
1. Methyl 2-(2'-hydroxy)phenyl propionate To a solution of 2-(2'-hydroxy)phenyl propionic acid (2 g; 12 mmol) (prepared according to methods known in the literature) in methyl alcohol (10 ml) a catalytic amount of conc. $H_2SO_4$ (3 drops) is added; the mixture is stirred at r.t. for 18 h. The solvent is then evaporated and the residual oil is taken up with ethyl ether (10 ml); the organic phase is then washed with $H_2O$ (3×10 ml), dried over $Na_2SO_4$ and evaporated to give 2.17 g (12 mmol) of methyl ester in the form of a transparent oil.

Quantitative Yield $^1$H-NMR ($CDCl_3$): δ 7.30-7.26 (m, 2H); 7.2-7.15 (m, 1H); 6.75 (d, 1H, J=7 Hz); 5.55 (bs, 1H, OH); 4.15 (q, 1H, J=7 Hz); 3.70 (s, 3H); 1.75 (d, 3H, J=7 Hz).

2. Methyl 2-[2'-(2"-chloro)-phenoxy]phenylpropionate

Methyl 2-(2'-hydroxy)phenylpropionate (2 g; 11.1 mmol) is dissolved in $CHCl_3$ (60 ml); 2-chlorophenyl boronic acid (7.71 g; 49.3 mmol), copper acetate (3.24 g; 17.82 mmol) and triethylamine (7.7 ml; 5.54 mmol) are added in sequence. The solution thus obtained is refluxed for 24 h, until the starting product disappears. After cooling at r.t. the salts are filtered off on a Celite cake; the filtrate is washed with 2N HCl (3×50 ml) and with a saturated solution of NaCl (2×35 ml); the organic phase is dried over $Na_2SO_4$ and is evaporated at reduced pressure to give a dark oily residue that is purified by means of flash-chromatography (eluent $CHCl_3$:$CH_3OH$ 9:1). Methyl 2-[2'(2"-chloro)phenoxy]phenylpropionate (1.38 g; 5 mmol) is recovered in the form of transparent oil.

Yield 45%

$^1$H-NMR ($CDCl_3$): δ 7.45-7.22 (m, 4H); 7.15-7.08 (m, 2H); 7.05-6.95 (m, 2H); 6.92-6.88 (m, 1H); 4.28 (q, 1H, J=7 Hz); 3.85 (s, 3H); 1.65 (d, 3H, J=7 Hz).

3. (R,S) 2-[2'-(2"-chloro)phenoxy]phenyl propionic acid

Methyl 2-[2'-(2"-chloro)phenoxy]phenylpropionate (1.3 g; 4.7 mmol) is dissolved in dioxan (15 ml). 1M NaOH (4.7 ml) is added to the solution and the solution is stirred at r.t. for 18 h. The solvent is evaporated at reduced pressure and the residue is taken up with water; the aqueous phase is taken to pH=1 with conc. $H_2SO_4$ conc. and extracted with $CHCl_3$ (3×15 ml). The combined organic extracts are washed with a saturated solution of $NaHCO_3$, then with a saturated solution of NaCl, dried over $Na_2SO_4$ and evaporated at reduced pressure to give (R,S) 2-[2'-(2"-chloro)phenoxy]phenyl]propionic acid (1.18 g; 4.5 mmol) as a clear yellow waxy solid.

Yield 96%

$^1$H-NMR ($CDCl_3$): δ 7.45-7.22 (m, 4H); 7.15-7.08 (m, 2H); 7.05-6.95 (m, 2H); 6.92-6.88 (m, 1H); 3.95 (q, 1H, J=7 Hz); 1.50 (d, 3H, J=7 Hz).

According to the same procedure the following compound was prepared

Example 25

(R,S) 2-[2'-(2",6"-dichloro)phenoxy]phenylpropionic acid $^1$H-NMR ($CDCl_3$): δ 9.40 (bs, 1H, COOH); 7.40-7.30 (d, 2H, J=8 Hz); 7.27-7.15 (m, 4H); 6.70-6.60 (d, 1H, J=8 Hz); 3.90 (q, 1H, J=7 Hz); 1.55 (d, 3H, J=7 Hz).

Example 26

Preparation of 2-(3-methylindane-5-yl)propanoic acid

Starting from 6-methoxy-1-indanone (commercial reagent) the required acid was synthesized according to methods known in the literature. In particular 6-methoxy-1-indanone was subjected to the Wittig reaction (yield 80%) with the ilide of triphenylmethylphosfonium bromide to give the esomethylene derivative that, by catalytic hydrogenation ($H_2$/Pd 5%, P atm.; yield 95%) was reduced to methyl indanoyl derivative. The substrate, by treatment with $BBr_3$, was deprotected on the phenolic group (yield>95%/o); by processing the intermediate with trifluoromethansulfonic anhydride the corresponding triflate was obtained (yield 80%) to be subjected to cross-coupling reaction (Stille reaction previously described) with the methyl 2-tributylstannylacrylate. The reaction proceeds with good yield (40%) and the 2-methoxycarbonyl isopropen-2-yl intermediate thus obtained, after catalytic hydrogenation for the reduction of the double bond and saponification in well known conditions with KOH/EtOH, allows to obtain 2-(3-methylindane-5-yl)propanoic acid with high yields.

Yield 90%

$^1$H-NMR (CDCl$_3$): δ 7.15-7.05 (m, 3H); 3.75 (m, 1H); 3.15 (m, 1H); 2.95-2.70 (m, 2H); 2.32 (m, 1H); 1.78-1.58 (m, 1H); 1.50 (d, 3H, J=7 Hz); 1.35 (d, 3H, J=7 Hz).

General Procedure for the Synthesis of (S) and (R)-2-[(4'-aryl/alkylsulfonylamino)phenyl]propionic acids of Formula Ia The separation of the two enantiomers of the commercial reagent 2-(4'-nitrophenyl)propionic acid is achieved by crystallisation of the corresponding S-(−) or R-(+)-α-phenylethylammonium salts in ethanolic solution as described in Akgun H. et al., Arzneim.-Forsch./Drug Res., 46(II), Nr. 9, 891-894 (1996).

(S)-2-(4'-nitrophenyl)propionic acid
[α]$_D$=+43.9° (c=2; abs. EtOH);
$^1$H-NMR (CDCl$_3$): δ 8.15 (d, 2H, J=7 Hz); 7.47 (d, 2H, J=7 Hz); 3.95 (bs, 1H, COOH); 3.78 (m, 1H); 1.52 (d, 3H, J=7 Hz).

(R)-2-(4'-nitrophenyl)propionic acid
[α]$_D$=−43.5° (c=2; abs. EtOH);
$^1$H-NMR (CDCl$_3$): δ 8.12 (d, 2H, J=7 Hz); 7.49 (d, 2H, J=7 Hz); 3.90 (bs, 1H, COOH); 3.81 (m, 1H); 1.50 (d, 3H, J=7 Hz).

4'-nitrophenylpropionic acids methyl esters (R)-2-(4'-nitrophenyl)propionic acid (4 mmol) is dissolved in methanol (40 mL) and 96% H$_2$SO$_4$ is added dropwise (0.5 mL). The resulting solution is left stirring overnight. After solvents evaporation the oily residue is dissolved in diethyl ether and the organic phase is washed with a sat. solution of NaHCO$_3$ (2×30 mL), dried over Na$_2$SO$_4$ and evaporated under reduced pressure to give the desired product as pale yellow oil.

(R)-2-(4'-nitrophenyl)propionic acid methyl ester
[α]$_D$=−48.3° (c=2; abs. EtOH);
$^1$H-NMR (CDCl$_3$): δ 8.12 (d, 2H, J=7 Hz); 7.49 (d, 2H, J=7 Hz); 3.75 (m, 1H); 3.70 (s, 3H); 1.51 (d, 3H, J=7 Hz).

(S)-2-(4'-nitrophenyl)propionic acid methyl ester
[α]$_D$=+49° (c=2; abs. EtOH);
$^1$H-NMR (CDCl$_3$): δ 8.11 (d, 2H, J=7 Hz); 7.49 (d, 2H, J=7 Hz); 3.78 (m, 1H); 3.68 (s, 3H); 1.51 (d, 3H, J=7 Hz).

(S) and (R)-2-(4'-aminophenyl)propionic acids methyl esters

Both the compounds are prepared by nitro group reduction as described in Ram S. et al., Tetrahedron Lett., 25, 3415 (1984) and in Barrett A. G. M. et al., Tetrahedron Lett., 29, 5733 (1988).

(S)-2-(4'-aminophenyl)propionic acid methyl ester
[α]$_D$=+16.5° (c=2; abs. EtOH);
$^1$H-NMR (CDCl$_3$): δ 7.85 (d, 2H, J=7 Hz); 7.45 (d, 2H, J=7 Hz); 3.81 (m, 1H); 3.67 (s, 3H); 1.62 (d, 3H, J=7 Hz).

(R)-2-(4'-aminophenyl)propionic acid methyl ester
[α]$_D$=−17.1° (c=2; abs. EtOH);
$^1$H-NMR (CDCl$_3$): δ 7.85 (d, 2H, J=7 Hz); 7.45 (d, 2H, J=7 Hz); 3.81 (m, 1H); 3.66 (s, 3H); 1.65 (d, 3H, J=7 Hz).

(R)-2-[(4'-aryl/alkylsulfonylamino)phenyl]propionic acids

To a solution of the above described (R)-2-(4'-aminophenyl)propionic acid methyl ester (10 mmol) in acetone (20 mL), dry pyridine (15 mmol) or equivalent organic/inorganic base and arylsulfonyl (or alkylsulfonyl) chloride (10 mmol) are added and the resulting solution is left stirring overnight. After solvent evaporation the oily residue is dissolved in CHCl$_3$ (30 mL) and the organic phase is washed with water (3×30 mL), dried over Na$_2$SO$_4$ and evaporated to give the desired product pure as solid after treatment at room temperature overnight in isopropyl ether and filtration under vacuum of the precipitate.

To a solution of the methyl ester (6 mmol) in CH$_3$OH (25 mL), 2N NaOH (12 mmol) is added and the resulting mixture is left stirring overnight at room temperature. CH$_3$OH is evaporated and the aqueous basic layer is acidified to pH=2 by dropping 12 N HCl; ethyl acetate is added and the two phases are separated. The organic extracts are washed back with water (3×20 mL), dried over Na$_2$SO$_4$ and evaporated under reduced pressure to give the product isolated pure as solid after treatment at room temperature overnight in n-hexane and filtration under vacuum of the precipitate (yield 75%-100%).

According the above described procedure the following compounds have been synthesised:

Example 27

(R) 2-(4'-(benzenesulfonylamino)phenylpropionic acid
[α]$_D$=−56.5° (c=1; abs. EtOH);
$^1$H-NMR (CDCl$_3$): δ 9.40 (bs, 1H, SO$_2$NH); 7.70 (d, 2H, J=8 Hz); 7.30 (m, 3H); 7.05 (d, 2H, J=8 Hz); 6.92 (d, 2H, J=8 Hz); 3.45 (q, 1H, J=7 Hz); 1.22 (d, 3H, J=7 Hz).

Example 28

(R) 2-(4'-methanesulfonylamino)phenylpropionic acid
[α]$_D$=−124.3° (c=1; abs. EtOH);
$^1$H-NMR (CDCl$_3$): δ 7.48 (bs, 1H, SO$_2$NH); 7.35 (d, 2H, J=8 Hz); 7.18 (d, 2H, 3=8 Hz); 6.55 (bs, 1H, SO$_2$NH); 3.80 (q, 1H, J=7 Hz); 3.00 (s, 3H); 1.55 (d, 3H, 37 Hz).

Example 29

(R) 2-[4'-(2"-propane)sulfonylamino]phenylpropionic acid
[α]$_D$=−110° (c=1; abs. EtOH);
$^1$H-NMR (CDCl$_3$): δ7.21 (d, 2H, J=8 Hz); 7.05 (d, 2H, J=8 Hz); 6.20 (bs, 1H, SO$_2$NH); 3.65 (q, 1H, J=7 Hz); 3.23 (m, 1H); 1.50 (d, 3H, J=7 Hz); 1.30 (d, 6H, J=7 Hz).

Example 30

(R) 2-(4'-trifluoromethanesulfonylamino)phenylpropionic acid
[α]$_D$=−84.5° (c=1; abs. EtOH);
$^1$H-NMR (CDCl$_3$): δ 7.25-7.05 (m, 4H); 7.00 (bs, 1H, SO$_2$NH); 3.60 (q, 1H, J=7 Hz); 1.41 (d, 3H, J=7 Hz).

Example 31

(R) 2-(4'-benzylsulfonylamino)phenylpropionic acid
[α]$_D$=−47° (c=1; abs. EtOH);
$^1$H-NMR (CDCl$_3$): δ 7.53 (m, 5H); 7.31 (d, 2H, J=7 Hz); 7.15 (bs, 1H, SO$_2$NH); 7.02 (d, 2H, J=7 Hz); 4.65 (s, 2H); 3.80 (m, 1H); 1.55 (d, 3H, J=7 Hz).

Example 32

(R) 2-[4'-(2"-chloro)benzenesulfonylamino]phenylpropionic acid
[α]$_D$=−81.5° (c=1; abs. EtOH);
$^1$H-NMR (CDCl$_3$): δ 7.95 (d, 1H, J=8 Hz); 7.40 (m, 2H); 7.22 (m, 1H); 7.10 (m, 2H); 6.95 (m, 2H+SO$_2$NH); 3.55 (q, 1H, J=7 Hz); 1.35 (d, 3H, J=7 Hz).

Example 33

(R) 2-[4'-(2"-ethyl)benzenesulfonylamino]phenylpropionic acid
Preparation of 2-ethylbenzenesulfonyl chloride Starting from commercial 2-ethylbenzenethiol, the related sulfonic acid is prepared as described in Trahanovsky W. S., "Oxidation in Organic Chemistry", Vol. 5-D, 201-203 Academic Press, Inc, (London), 1982. Treatment of the sulfonic acid with excess thionyl chloride gives the 2-ethylbenzenesulfonyl chloride pure to be used in the condensation with R(−)-2-(4'-aminophenyl)propionic acid methyl ester.

$[\alpha]_D$=−95° (c=1; abs. EtOH);
$^1$H-NMR (CDCl$_3$): δ 9.30 (bs, 1H, SO$_2$NH); 7.70 (d, 2H, J=8 Hz); 7.25 (m, 4H); 7.08 (d, 2H, J=8 Hz); 3.41 (q, 1H, J=7 Hz); 2.70 (q, 2H, J=8 Hz); 1.42 (d, 3H, J=8 Hz); 1.22 (d, 3H, J=7 Hz).

Example 34

(R) 2-(4'-aminosulfonylamino)phenylpropionic acid
$[\alpha]_D$=−110° (c=1; abs. EtOH);
$^1$H-NMR (CDCl$_3$): δ 7.95 (d, 2H, J=8 Hz); 7.54 (bs, 2H, NSO$_2$NH$_2$); 6.98 (m, 2H+SO$_2$NH); 3.57 (q, 1H, J=7 Hz); 1.30 (d, 3H, J=7 Hz).

General Procedure for the Synthesis of (S) and (R)-2-[(4'-aryl/alkylsulfonyloxy)phenyl]propionic Acids of Formula Ia The separation of the two enantiomers of the commercial reagent 2-(4'-hydroxyphenyl)propionic acid is achieved by crystallisation of the corresponding S(−) or R(+)-α-phenylethylammonium salts in ethanolic solution as described in Akgun H. et al., Arzneim.-Forsch./Drug Res., 46(II), Nr. 9, 891-894 (1996).

(S)-2-(4'-hydroxyphenyl)propionic acid
$[\alpha]_D$=+12° (c=2; abs. EtOH);
$^1$H-NMR (CDCl$_3$): δ 7.31 (d, 2H, J=7 Hz); 7.05 (d, 2H, J=7 Hz); 6.25 (bs, 1H, OH); 3.80 (q, 1H, J=7 Hz); 1.52 (d, 3H, J=7 Hz).

(R)-2-(4'-hydroxyphenyl)propionic acid
$[\alpha]_D$=−12.5° (c=2; abs. EtOH);
$^1$H-NMR (CDCl$_3$): δ 7.30 (d, 2H, J=7 Hz); 7.07 (d, 2H, J=7 Hz); 6.35 (bs, 1H, OH); 3.75 (q, 1H, J=7 Hz); 1.50 (d, 3H, J=7 Hz).

(R) and (S)-2-(4'-hydroxyphenyl)propionic acid methyl esters (2R)-2-(4'-hydroxyphenyl)propionic acid (4 mmol) is dissolved in CH$_3$OH (40 mL) and conc. H$_2$SO$_4$ is added dropwise (0.5 mL). The resulting solution is left stirring overnight. After solvents evaporation the oily residue is dissolved in diethyl ether and the organic phase is washed with a sat. solution of NaHCO$_3$ (2×30 mL), dried over Na$_2$SO$_4$ and evaporated under reduced pressure to give the desired product as pale yellow oil.

(R) 2-(4'-hydroxyphenyl)propionic acid methyl ester
$[\alpha]_D$=−78° (c=2; abs. EtOH);
$^1$H-NMR (CDCl$_3$): δ 7.32 (d, 2H, J=7 Hz); 7.10 (d, 2H, J=7 Hz); 6.40 (bs, 1H, OH); 3.70 (m, 4H); 1.53 (d, 3H, J=7 Hz).

(R) 2-[(4'-aryl/alkylsulfonyloxy)phenyl]propionic acids

A mixture of the above described (2R)-2-(4'-hydroxyphenyl)propionic acid methyl ester (2 mmol) and arylsulfonyl (or alkylsulfonyl) chloride (2 mmol) in dry pyridine (1 mL) or in presence of equivalent organic/inorganic base is warmed at T=60° C. for 24 hours. After cooling at room temperature the reaction mixture is poured into 1 N HCl (5 mL) and the aqueous solution is extracted with CH$_2$Cl$_2$ (3×10 mL). The collected organic extracts are washed back with 1N NaOH (2×10 mL), dried over Na$_2$SO$_4$ and evaporated under reduced pressure to give a crude residue pure enough to be used for the following step (yield 80-92%).

A mixture of the crude methyl ester (1.85 mmol), glacial acetic acid (2.5 mL) and 37% HCl (0.5 mL) is refluxed for 18 hours. All the solvents are evaporated off, the oily residue is dissolved in CH$_2$Cl$_2$ (5 mL) and the organic phase is washed with 1N NaOH (2×5 mL) and with water (2×10 mL), dried over Na$_2$SO$_4$ and evaporated under reduced pressure to give pure (2R) aryl (or alkyl)sulfonyloxyphenyl propionic acids in a quantitative yield According the above described procedure the following compounds have been synthesised:

Example 35

(R) 2-(4'-benzenesulfonyloxy)phenylpropionic acid
$[\alpha]_D$=−66.20 (c=1; abs. EtOH);
$^1$H-NMR (CDCl$_3$): δ 7.92 (d, 2H, J=7 Hz); 7.70 (t, 1H, J=7 Hz); 7.57 (t, 2H, J=7 Hz); 7.25 (d, 2H, J=7 Hz); 6.95 (d, 2H, J=7 Hz); 3.75 (q, 1H, J=7 Hz); 1.50 (d, 3H, J=7 Hz).

Example 36

(R) 2-(4'-benzylsulfonyloxy)phenylpropionic acid
$[\alpha]_D$=−84.6° (c=1; abs. EtOH);
$^1$H-NMR (CDCl$_3$): δ 7.50 (m, 5H); 7.28 (d, 2H, J=7 Hz); 7.05 (d, 2H, J=7 Hz); 4.53 (s, 2H); 3.77 (m, 1H); 1.52 (d, 3H, J=7 Hz).

Example 37

(R) 2-(4'-trifluoromethanesulfonyloxy)phenylpropionic acid
$[\alpha]_D$=−28.50 (c=1; CH$_3$OH);
$^1$H-NMR (CDCl$_3$): δ 7.45 (d, 2H, J=7 Hz); 7.22 (d, 2H, J=7 Hz); 3.82 (q, 1H, J=7 Hz); 1.51 (d, 3H, J=7 Hz).

Example 38

(R) 2-[4'-(2"-propane)sulfonyloxy]phenylpropionic acid
$[\alpha]_D$=−42.8° (c=1; CH$_3$OH);
$^1$H-NMR (CDCl$_3$): δ 7.41 (d, 2H, J=7 Hz); 7.25 (d, 2H, J=7 Hz); 3.82 (q, 1H, J=7 Hz); 3.45 (q, 1H, J=7 Hz); 1.52 (m, 9H).

Example 39

(R) 2-[4'-(2"-chloro)benzenesulfonyloxy]phenylpropionic acid
$[\alpha]_D$=−43° (c=1; abs. EtOH);
$^1$H-NMR (CDCl$_3$): δ 7.90 (d, 1H, J=8 Hz); 7.44 (m, 2H); 7.20 (m, 1H); 7.12 (m, 2H); 6.95 (d, 2H, J=8 Hz); 3.52 (q, 1H, J=7 Hz); 1.38 (d, 3H, J=7 Hz).

Example 40

(R) 2-[4'-(2"-ethyl)benzenesulfonyloxy]phenylpropionic acid
Preparation of 2-ethylbenzenesulfonyl chloride Starting from commercial 2-ethylbenzenethiol, the related sulfonic acid is prepared as described in Trahanovsky W. S., "Oxidation in Organic Chemistry", Vol. 5-D, 201-203 Academic Press, Inc, (London), 1982. Treatment of the sulfonic acid with excess thionyl chloride gives the 2-ethylbenzenesulfonyl chloride pure to be used in the condensation with (R)-2-(4'-hydroxyphenyl)propionic acid methyl ester.

$[\alpha]_D = -1040$ (c=1; abs. EtOH);
$^1$H-NMR (CDCl$_3$): δ 7.71 (d, 2H, J=8 Hz); 7.25 (m, 4H); 7.12 (d, 2H, J=8 Hz); 3.44 (q, 1H, J=7 Hz); 2.71 (q, 2H, J=8 Hz); 1.45 (d, 3H, J=8 Hz); 1.20 (d, 3H, J=7 Hz).

Example 41

(R) 2-(4'-aminosulfonyloxy)phenylpropionic acid
$[\alpha]_D = -91.5°$ (c=1; abs. EtOH);
$^1$H-NMR (CDCl$_3$): δ 7.95 (d, 2H, J=8 Hz); 7.84 (bs, 2H, NSO$_2$NH$_2$); 6.95 (d, 2H, J=8 Hz); 3.61 (q, 1H, J=7 Hz); 1.35 (d, 3H, J=7 Hz).

Procedure for the Synthesis of (S) and (R)-2-[(4'-aryl/alkyl-sulfonylmethyl)phenyl]propionic acids of Formula Ia

Example 42

(R) 2-(4'-benzenesulfonylmethyl)phenylpropionic acid

The title product is prepared by a multi-step synthesis starting from the commercial (R)-2-phenylpropionic acid. Following the procedure described in EP 0 889 020 (Ex. 4), (R)-2-[(4'-chloromethyl)phenyl]propionic acid is prepared in good yield. The acid is transformed into the methyl ester by usual procedure and the ester is added to a cooled mixture of benzenethiol/potassium tert-butoxide/18-crown-6 (1:1.1:0.95) and, after overnight reaction and usual work-up (washings with water, drying over Na$_2$SO$_4$ and solvent evaporation), the pure benzenethiomethyl derivative is isolated and used in the following oxidative step. The oxidation to the related sulfone by 2 equivalents of 3-chloroperoxybenzoic acid and the final treatment with NaOH/dioxane at room temperature allow to isolate the desired product in good final yield (65% starting from (R)-2-[(4'-chloromethyl)phenyl]propionic acid).

$[\alpha]_D = -125°$ (c=1; abs. EtOH);
$^1$H-NMR (CDCl$_3$): δ 7.90 (m, 2H); 7.44-7.20 (m, 3H); 7.12 (d, 2H, J=8 Hz); 6.95 (d, 2H, J=8 Hz); 3.72 (s, 2H); 3.55 (q, 1H, J=7 Hz); 1.43 (d, 3H, J=7 Hz).

Example 43

(R) 2-(4'-trifluoromethanesulfonylmethyl)phenylpropionic acid

Following the procedure described in U.S. Pat. No. 5,245,039 (14 Sep. 1993) and starting from (R)-2-[(4'-chloromethyl)phenyl]propionic acid methyl ester, the related (R)-2-[(4'-thiomethyl)phenyl]propionic acid is obtained in high yield (85%). By treatment of the thiolate ("in situ" generated with 1 equivalent of potassium tert-butoxide) with the commercial trifluoromethyl iodide, the trifluoromethanethiomethyl derivative is obtained. The following oxidation to the sulfone derivative (by treatment with 2 equivalents of 3-chloroperoxybenzoic acid) and the final ester hydrolysis by NaOH/dioxane at room temperature allow to isolate the desired product in quite good final yield (47% starting from (R)-2-[(4'-chloromethyl)phenyl]propionic acid).

$[\alpha]_D = -86°$ (c=1; abs. EtOH);
$^1$H-NMR (CDCl$_3$): δ 7.14 (d, 2H, J=8 Hz); 7.02 (d, 2H, J=8 Hz); 3.85 (s, 2H); 3.51 (q, 1H, J=7 Hz); 1.48 (d, 3H, J=7 Hz).

List of the Examples Structures

| Example | Structure formula |
|---------|-------------------|
| 1 | 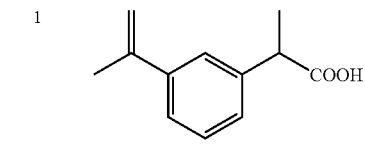 |
| 2 | 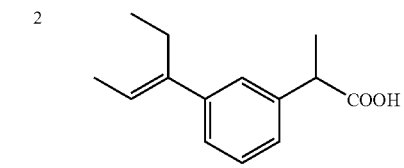 |
| 3 | 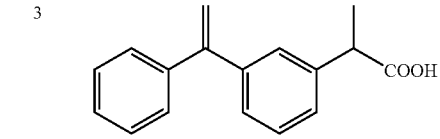 |
| 4 | 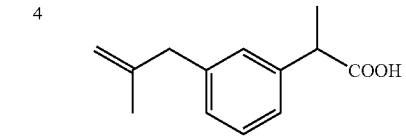 |
| 5 | 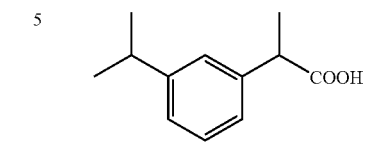 |
| 6 | 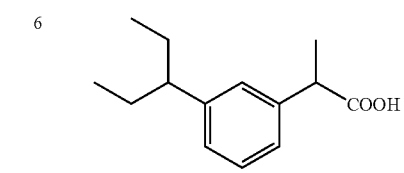 |
| 7 | 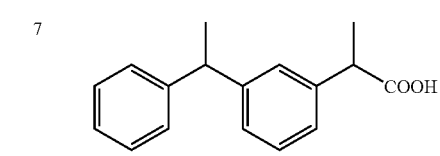 |
| 8 | 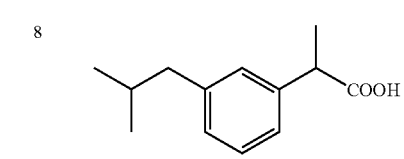 |

| Example | Structure formula |
|---|---|
| 9 | 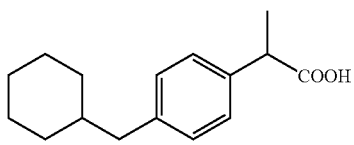 |
| 10 | 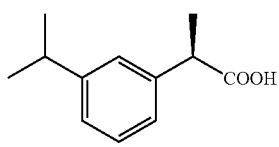 |
| 11 | 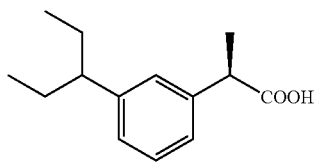 |
| 12 | 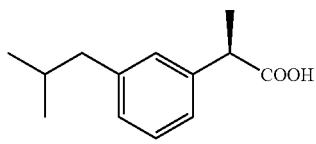 |
| 13 | 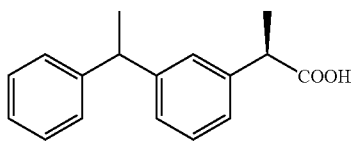 |
| 14 | 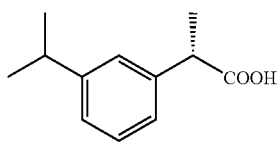 |
| 15 | 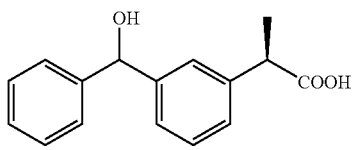 |
| 16 | 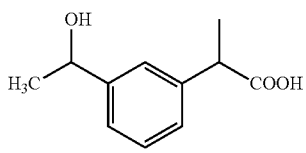 |
| 17 | 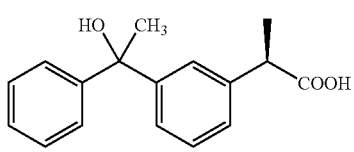 |
| Example | Structure formula |
|---|---|
| 18 | 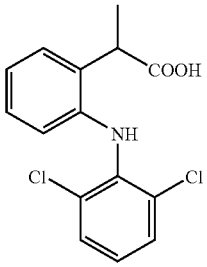 |
| 19 | 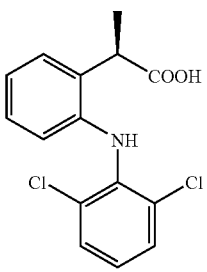 |
| 20 | 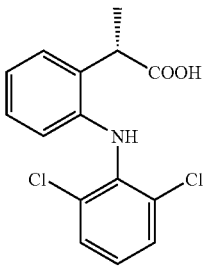 |
| 21 | 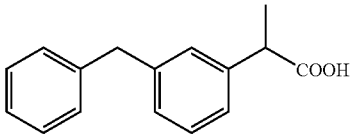 |
| 22 | 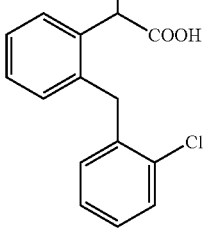 |
| 23 | 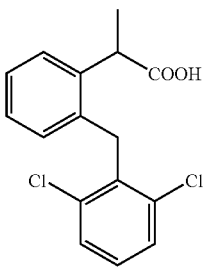 |

| Example | Structure formula |
|---|---|
| 24 | 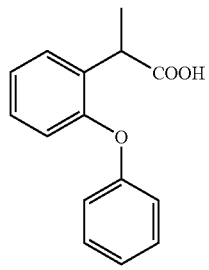 |
| 25 | 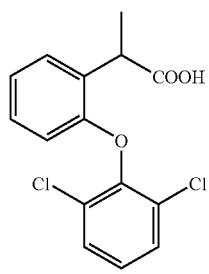 |
| 26 | 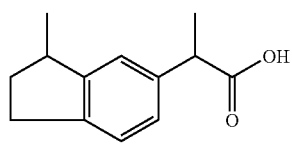 |
| 27 | 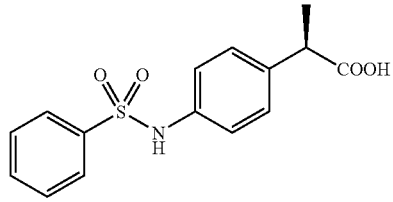 |
| 28 | 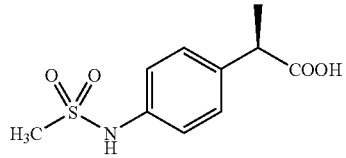 |
| 29 | 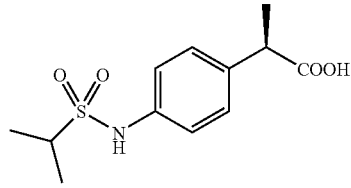 |
| 30 | 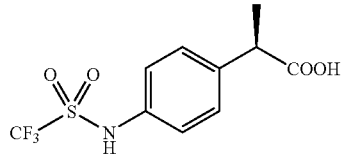 |
| 31 | 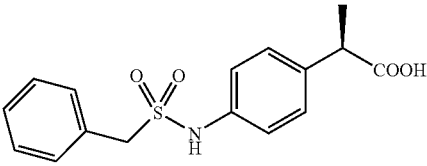 |
| 32 | 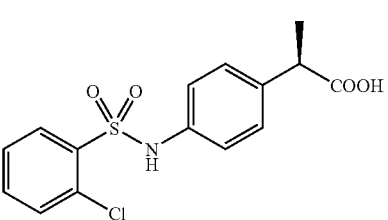 |
| 33 | 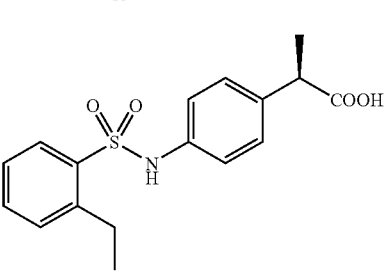 |
| 34 | 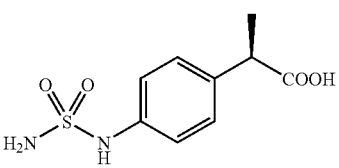 |
| 35 | 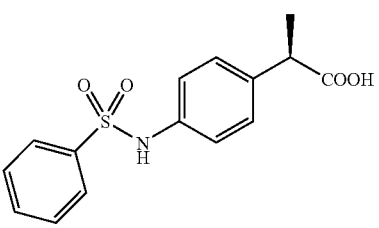 |
| 36 | 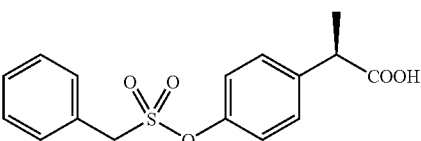 |
| 37 | 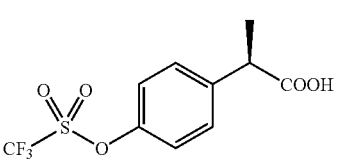 |
| 38 | 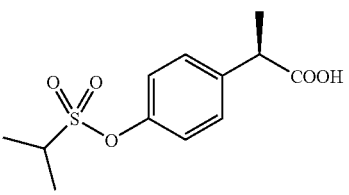 |

-continued

| Example | Structure formula |
|---|---|
| 39 | 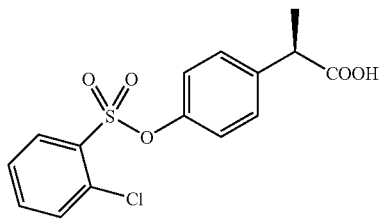 |
| 40 | 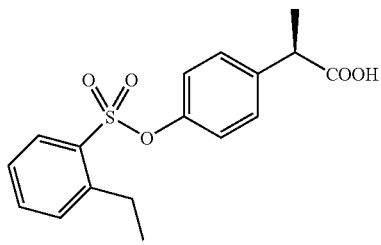 |
| 41 | 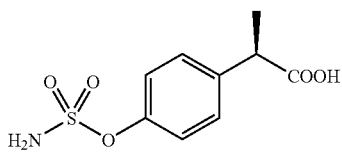 |
| 42 | 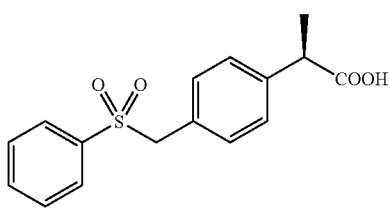 |
| 43 | 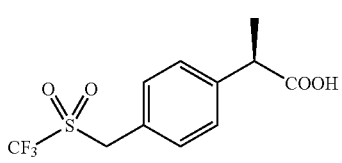 |

The invention claimed is:

1. A method for the treatment of psoriasis, ulcerative colitis, melanoma, chronic obstructive pulmonary disease (COPD), bollous pemphigo, idiopathic fibrosis, glomerulonephritis and for the treatment of damage caused by ischemia and reperfusion, which comprises:
administering to a patient in need thereof an effective amount of a (R,S)-2-aryl-propionic acid compound of formula (I), or the single (R) or (S) enantiomer:

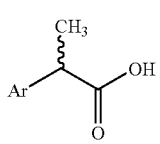

or a pharmaceutically acceptable salt thereof,
wherein Ar is a phenyl ring substituted by:
a group in the 3 (meta) position selected from a linear or branched $C_1$-$C_5$ alkyl, $C_2$-$C_5$-alkenyl or $C_2$-$C_5$-alkynyl group optionally substituted by $C_1$-$C_5$-alkoxycarbonyl, substituted or not-substituted phenyl, linear or branched $C_1$-$C_5$ hydroxyalkyl, aryl-hydroxymethyl, or
a group in the 3 (meta) position selected from a linear or branched $C_1$-$C_5$ alkyl group, optionally substituted by $C_1$-$C_5$-alkoxycarbonyl, substituted or not-substituted phenyl, linear or branched $C_1$-$C_5$ hydroxyalkyl, aryl-hydroxymethyl, together with a substituent in the ortho or para position that comprises a benzene ring or a saturated or unsaturated, substituted or non-substituted bicycloaryl group; or
a group in the 4 (para) position selected from $C_1$-$C_5$-acyloxy, substituted or not-substituted benzoyloxy, $C_1$-$C_5$-acylamino, substituted or not-substituted benzoylamino, $C_1$-$C_5$-sulfonyloxy, substituted or not-substituted benzenesulfonyloxy, $C_1$-$C_5$-alkanesulfonylamino, substituted or not-substituted benzenesulfonylamino, $C_1$-$C_5$-alkanesulfonylmethyl, substituted or not-substituted benzenesulfonylmethyl, $C_3$-$C_6$-cycloalkyl, 2-furyl, 3-tetrahydrofuryl, 2-thiophenyl, 2-tetrahydrothiophenyl, $C_1$-$C_8$ (alkanoyl)-$C_1$-$C_5$-alkylamino, $C_1$-$C_8$ (cycloalkanoyl)-$C_1$-$C_5$-alkylamino or $C_1$-$C_8$ (arylalkanoyl)-$C_1$-$C_5$-alkylamino; or
a group in the 2 (ortho) position selected from substituted or not-substituted arylmethyl, substituted or not-substituted aryloxy, or substituted or not-substituted arylamino, wherein the substituents of the aryl group are selected from $C_1$-$C_4$ alkyl, $C_1$-$C_4$-alkoxy, chlorine, fluorine and/or trifluoromethyl groups, with the exception of (R,S)-2-(2'-benzylphenyl)-propionic acid.

2. The method of claim 1, wherein Ar is:
a phenyl ring 3-substituted by a group selected from: isoprop-1-en-1-yl, ethyl, isopropyl, pent-2-en-3-yl, pent-3-yl, 1-phenyl-ethylen-1-yl, α-methylbenzyl, α-hydroxybenzyl, α-hydroxyethyl, α-hydroxypropyl, or a bicyclic aryl group;
or Ar is a phenyl ring 4-substituted by a group selected from: trifluoromethanesulfonyloxy, 2-propanesulfonyloxy, benzylsulfonyloxy, benzenesulfonyloxy, 2'-ethylbenzenesulfonyloxy, 2'-chlorobenzenesulfonyloxy, methanesulfonylamino, trifluoromethanesulfonylamino, 2-propanesulfonylamino, benzylsulfonylamino, benzenesulfonylamino, 2'-ethylbenzenesulfonylamino, aminosulfonylmethyl, 2'-chlorobenzenesulfonylamino, trifluoromethanesulfonylmethyl, benzenesulfonylmethyl, aminosulfonyloxy, or aminosulfonylamino;
or Ar is a phenyl ring 2-substituted by a group selected from: 2-(2,6-dichloro-phenylamino)-phenyl, 2-(2,6-dichloro-phenyl-amino)-5-chloro-phenyl, 2-(2,6-dichloro-3-methyl-phenyl-amino)-phenyl, 2-(3-trifluoromethyl-phenyl-amino)-phenyl, 2-(2,6-dichloro-phenoxy)-phenyl, 2-(2-chloro-phenoxy)-phenyl, 2-(2,6-dichloro-benzyl)-phenyl, or 2-(2-chloro-benzyl)-phenyl.

3. The method of claim 2, wherein said compound is selected from the group consisting of:
(R,S) 2-[3'-(alpha-ethyl-propyl)phenyl]propionic acid,
(R) 2-[3'-(alpha-ethyl-propyl)phenyl]propionic acid,
(S) 2-[3'-(alpha-ethyl-propyl)phenyl]propionic acid,
2-[3'-(alpha-hydroxy-ethyl)phenyl]propionic acid, and the single diastereoisomers thereof,
2-[3'-(alpha-hydroxy-propyl)phenyl]propionic acid and the single diastereoisomers thereof,
(R,S) 2-[3'-isopropylphenyl]propionic acid,
(R) 2-[3'-isopropylphenyl]propionic acid,
(S) 2-[3'-isopropylphenyl]propionic acid, (R) 2-(4'-trifluoromethanesulfonyloxy)phenylpropionic acid,
(S) 2-(4'-trifluoromethanesulfonyloxy)phenylpropionic acid,
(R) 2-(4'-benzenesulfonyloxy)phenylpropionic acid,
(S) 2-(4'-benzenesulfonyloxy)phenylpropionic acid,
(R) 2-[4'-(2''-ethyl)benzenesulfonyloxy]phenylpropionic acid,
(S) 2-[4'-(2''-ethyl)benzenesulfonyloxy]phenylpropionic acid,
(R) 2-[4'-(2''-chloro)phenylsulfonyloxy]phenylpropionic acid,
(S) 2-[4'(2''-chloro)phenylsulfonyloxy]phenylpropionic acid,
(R) 2-[4'-(2''-propane)sulfonyloxy]phenylpropionic acid,
(S) 2-[4'-(2''-propane)sulfonyloxy]phenylpropionic acid,
(R) 2-(4'-benzylsulfonyloxy)phenylpropionic acid,
(S) 2-(4'-benzylsulfonyloxy)phenylpropionic acid,
(R) 2-(4'-aminosulfonyloxy)phenylpropionic acid,
(S) 2-(4'-aminosulfonyloxy)phenylpropionic acid,
(R) 2-(4'-trifluoromethanesulfonylamino)phenylpropionic acid,
(S) 2-(4'-trifluoromethanesulfonylamino)phenylpropionic acid,
(R) 2-(4'-methanesulfonylamino)phenylpropionic acid,
(S) 2-(4'-methanesulfonylamino)phenylpropionic acid,
(R) 2-[4'-(2''-propane)sulfonylamino]phenylpropionic acid,
(S) 2-[4'-(2''-propane)sulfonylamino]phenylpropionic acid,
(R) 2-(4'-benzenesulfonylamino)phenylpropionic acid,
(S) 2-(4'-benzenesulfonylamino)phenylpropionic acid,
(R) 2-[4'-(2''-ethyl)benzenesulfonylamino]phenylpropionic acid,
(S) 2-[4'-(2''-ethyl)benzenesulfonylamino]phenylpropionic acid,
(R) 2-[4'-(2''-chloro)benzenesulfonylamino]phenylpropionic acid,
(S) 2-[4'-(2''-chloro)benzenesulfonylamino]phenylpropionic acid,
(R) 2-(4'-benzylsulfonylamino)phenylpropionic acid,
(S) 2-(4'-benzylsulfonylamino)phenylpropionic acid,
(R) 2-(4'-aminosulfonylamino)phenylpropionic acid,
(S) 2-(4'-aminosulfonylamino)phenylpropionic acid,
(R) 2-(4'-trifluoromethanesulfonylmethyl)phenylpropionic acid,
(S) 2-(4'-trifluoromethanesulfonylmethyl)phenylpropionic acid,
(R) 2-(4'-benzenesulfonylmethyl)phenylpropionic acid, and
(S) 2-(4'-benzenesulfonylmethyl)phenylpropionic acid.

4. The method according to claim 1, which comprises administering to a subject in need thereof an effective amount of a (R,S)-2-aryl-propionic acid compound of formula (Ia) or the single (R) or (S) enantiomer

(Ia)

or a pharmaceutically acceptable salt thereof, wherein Ar is a phenyl ring substituted in the 4 (para) position with a group selected from $C_1$-$C_5$-sulfonyloxy, substituted or not-substituted benzenesulfonyloxy, $C_1$-$C_5$-alkanesulfonylamino, substituted or not-substituted benzenesulfonylamino, $C_1$-$C_5$-alkanesulfonylmethyl, substituted or not-substituted benzenesulfonylmethyl.

5. The method of claim 3, wherein said compound is in admixture with a suitable carrier thereof.

6. A method for inhibiting IL-8 induced chemotaxis of human polymorphonucleated neutrophils and contemporaneously not inhibiting cyclooxygenase activity in a subject, which comprises administering to said subject in need thereof an effective amount of a (R,S)-2-aryl-propionic acid compound of formula (I) or the single (R) and (S) enantiomer

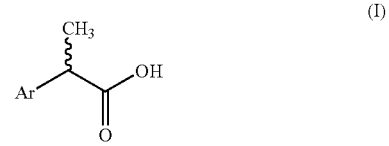

(I)

or a pharmaceutically acceptable salt thereof,
wherein Ar is a phenyl ring substituted by:
  a group in the 3 (meta) position selected from a linear or branched $C_1$-$C_5$ alkyl, $C_2$-$C_5$-alkenyl or $C_2$-$C_5$-alkynyl group optionally substituted by $C_1$-$C_5$-alkoxycarbonyl, substituted or not-substituted phenyl, linear or branched $C_1$-$C_5$ hydroxyalkyl, aryl-hydroxymethyl, or
  a group in the 3 (meta) position selected from a linear or branched $C_1$-$C_5$ alkyl group, optionally substituted by $C_1$-$C_5$-alkoxycarbonyl, substituted or not-substituted phenyl, linear or branched $C_1$-$C_5$ hydroxyalkyl, aryl-hydroxymethyl, together with a substituent in the ortho or para position that comprises a benzene ring or a saturated or unsaturated, substituted or non-substituted bicycloaryl group; or
  a group in the 4 (para) position selected from $C_1$-$C_5$-acyloxy, substituted or not-substituted benzoyloxy, $C_1$-$C_5$-acylamino, substituted or not-substituted benzoylamino, $C_1$-$C_5$-sulfonyloxy, substituted or not-substituted benzenesulfonyloxy, $C_1$-$C_5$-alkanesulfonylamino, substituted or not-substituted benzenesulfonylamino, $C_1$-$C_5$-alkanesulfonylmethyl, substituted or not-substituted benzenesulfonylmethyl, $C_3$-$C_6$-cycloalkyl, 2-furyl, 3-tetrahydrofuryl, 2-thiophenyl, 2-tetrahydrothiophenyl, $C_1$-$C_5$ (alkanoyl)-$C_1$-$C_5$-alkylamino, $C_1$-$C_8$ (cycloalkanoyl)-$C_1$-$C_5$-alkylamino or $C_1$-$C_8$ (arylalkanoyl)-$C_1$-$C_5$-alkylamino; or
  a group in the 2 (ortho) position selected from substituted or not-substituted arylmethyl, substituted or not-substituted aryloxy, or substituted or not-substituted acylamino, wherein the substituents of the aryl group are selected from $C_1$-$C_4$ alkyl, $C_1$-$C_4$-alkoxy, chlorine, fluorine and/or trifluoromethyl groups, with the exception of (R,S)-2-(2'-benzylphenyl)-propionic acid.

7. The method of claim 1, wherein the compound, enantiomer or pharmaceutically acceptable salt of the compound of formula (I) is one in which the Ar group is substituted at the 4 position by an acetyl-N-methyl-amino group or a pivaloyl-N-ethyl-amino group.

8. The method of claim 2, wherein Ar is a phenyl ring 3-substituted by a 3-methyl-indan-5-yl group, 3-methyl-indan-7-yl group, 8-methyl-tetrahydronaphth-2-yl group or a 5-methyl-tetrahydronaphth-1-yl group.

9. The method of claim 6, wherein the compound, enantiomer or pharmaceutically acceptable salt of the compound of formula (I) is one in which the Ar group is substituted at the 4 position by an acetyl-N-methyl-amino group or a pivaloyl-N-ethyl-amino group.

10. The method of claim 6, wherein Ar is a phenyl ring 3-substituted by a 3-methyl-indan-5-yl group, 3-methyl-indan-7-yl group, 8-methyl-tetrahydronaphth-2-yl group or a 5-methyl-tetrahydronaphth-1-yl group.

* * * * *